(12) United States Patent
Stelmach et al.

(10) Patent No.: US 7,687,534 B2
(45) Date of Patent: Mar. 30, 2010

(54) GLUCAGON RECEPTOR ANTAGONIST COMPOUNDS, COMPOSITIONS CONTAINING SUCH COMPOUNDS AND METHODS OF USE

(75) Inventors: John E. Stelmach, Westfield, NJ (US); Emma R. Parmee, Scotch Plains, NJ (US); James R. Tata, Westfield, NJ (US); Keith G. Rosauer, Laurence Harbor, NJ (US); Ronald M. Kim, Summit, NJ (US); Amy R. Bittner, Scotch Plains, NJ (US); Jiang Chang, Westfield, NJ (US); Christopher Joseph Sinz, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 184 days.

(21) Appl. No.: 11/906,374

(22) Filed: Oct. 2, 2007

(65) Prior Publication Data

US 2008/0085926 A1 Apr. 10, 2008

(51) Int. Cl.
*A61K 31/404* (2006.01)
*C07D 209/14* (2006.01)
(52) U.S. Cl. ...................... 514/415; 548/511
(58) Field of Classification Search ............ 514/415; 548/511
See application file for complete search history.

(56) References Cited

U.S. PATENT DOCUMENTS

| 5,776,954 | A | 7/1998 | de Laszlo et al. |
| 6,503,949 | B1 | 1/2003 | Lau et al. |
| 6,765,009 | B2 | 7/2004 | Francesco et al. |
| 2003/0158226 | A1 | 8/2003 | Belloni et al. |

FOREIGN PATENT DOCUMENTS

| EP | 1 489 077 | 12/2004 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03/053938 | 7/2003 |
| WO | WO 03/064404 | 8/2003 |
| WO | WO 03/097619 | 11/2003 |
| WO | WO 2004/002480 | 1/2004 |
| WO | WO 2006/102067 | 9/2006 |

OTHER PUBLICATIONS

Byrn et al. Solid-State Chemistry of Drugs, 2d, Chapter 11 Hydrates and Solvates, 233-247.*
Morissette et al. Adv. Drug Delivery Rev. 2004, 56, 275-300.*
A.M. Rouhi, Chem. & Eng. News, Feb. 24, 2003, 81(8), 32-35.*
Ling et al. Expert Opin. Ther. Patents 2003, 13(1), 15-22.*
Sloop et al. Expert Opin. Ther. Targets 2005, 9(3), 593-600.*
GlaxoSmithKline, "Glucagon Receptor Antagonists for the Treatment of Type 2 Diabetes", 226th ACS National Meeting, Abs. MEDI-164 (2003).
R. Kurukulasuriya et al., "Biaryl amide glucagon receptor antagonists", Bioorganic & Medicinal Chemistry Letters, vol. 14, pp. 2047-2050 (2004).

* cited by examiner

*Primary Examiner*—Rebecca L Anderson
*Assistant Examiner*—Jason Nolan
(74) *Attorney, Agent, or Firm*—Richard C. Billups; Catherine D. Fitch

(57) ABSTRACT

Glucagon receptor antagonist compounds are disclosed. The compounds are useful for treating type 2 diabetes and related conditions. Pharmaceutical compositions and methods of treatment are also included.

20 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

A compound represented by formula I:

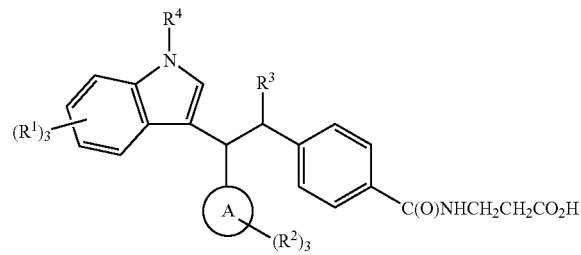

or a pharmaceutically acceptable salt or solvate thereof wherein:

ring A represents a phenyl or naphthyl group;

each $R^1$ and $R^2$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^3$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy, and $R^4$ represents H or $C_{1-4}$alkyl optionally substituted with 1-3 halo atoms up to perhalo and 1 phenyl ring.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Halogen" (Halo) includes fluorine, chlorine, bromine and iodine.

One aspect of the invention relates to a compound represented by formula I:

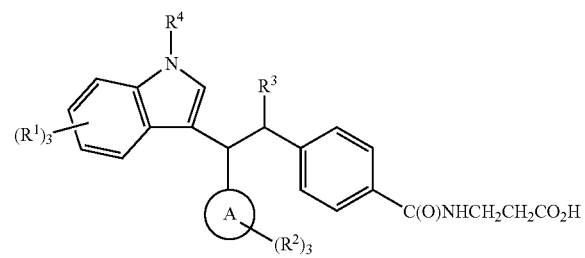

or a pharmaceutically acceptable salt or solvate thereof wherein:

ring A represents a phenyl or naphthyl group;

each $R^1$ and $R^2$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^3$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy, and $R^4$ represents H or $C_{1-4}$alkyl optionally substituted with 1-3 halo atoms up to perhalo and 1 phenyl ring.

One aspect of the invention that is of interest relates to compounds of formula I or a pharmaceutically acceptable salt or solvate thereof wherein ring A represents phenyl. Within this aspect of the invention, all other variables are as originally defined with respect to formula I.

Another aspect of the invention that is of interest relates to compounds of formula I or a pharmaceutically acceptable salt or solvate thereof wherein ring A represents naphthyl. Within this aspect of the invention, all other variables are as originally defined with respect to formula I.

Another aspect of the invention that is of interest relates to compounds of formula I or a pharmaceutically acceptable salt or solvate thereof wherein each $R^1$ represents H or is selected from the group consisting of halo selected from fluoro and chloro; $SCH_3$; CN, $C_{1-6}$alkyl, $C_{2-4}$alkenyl and $C_{1-6}$alkoxy, the alkyl and alkenyl portions of $SCH_3$, $C_{1-6}$alkyl, $C_{2-4}$alkenyl and $C_{1-6}$alkoxy being optionally substituted with 1-3 fluoro atoms. Within this aspect of the invention, all other variables are as originally defined with respect to formula I.

More particularly, an aspect of the invention that is interest relates to compounds of formula I or a pharmaceutically acceptable salt or solvate thereof wherein each $R^1$ represents H or is selected from the group consisting of fluoro, chloro; $SCH_3$; CN, $C_{1-4}$alkyl and $OCH_3$, the alkyl portions of $SCH_3$, $C_{1-4}$alkyl and $OCH_3$ being optionally substituted with 1-3 fluoro atoms. Within this aspect of the invention, all other variables are as originally defined with respect to formula I.

Another aspect of the invention that is of interest relates to compounds of formula I or a pharmaceutically acceptable salt or solvate thereof wherein each $R^2$ represents H or is selected from the group consisting of halo selected from fluoro and chloro; $SCH_3$; CN, $C_{1-6}$alkyl, $C_{2-4}$alkenyl and $C_{1-6}$alkoxy, the alkyl and alkenyl portions of $SCH_3$, $C_{1-6}$alkyl, $C_{2-4}$alkenyl and $C_{1-6}$alkoxy being optionally substituted with 1-3 fluoro atoms. Within this aspect of the invention, all other variables are as originally defined with respect to formula I.

More particularly, an aspect of the invention that is interest relates to compounds of formula I or a pharmaceutically acceptable salt or solvate thereof wherein each $R^2$ represents H or is selected from the group consisting of fluoro, chloro; $SCH_3$; CN, $C_{1-4}$alkyl and $OCH_3$, the alkyl portions of $SCH_3$, $C_{1-4}$alkyl and $OCH_3$ being optionally substituted with 1-3 fluoro atoms. Within this aspect of the invention, all other variables are as originally defined with respect to formula I.

Another aspect of the invention that is of interest relates to compounds of formula I or a pharmaceutically acceptable salt or solvate thereof wherein $R^3$ represents a member selected from the group consisting of: $CH_3$, ethyl, n-propyl, n-, s- and t-butyl, and allyl. Within this aspect of the invention, all other variables are as originally defined with respect to formula I.

Another aspect of the invention that is of interest relates to compounds of formula I or a pharmaceutically acceptable salt or solvate thereof wherein $R^4$ is selected from the group consisting of: H, Me, Et, n-propyl, n-butyl and benzyl. Within this aspect of the invention, all other variables are as originally defined with respect to formula I.

A particular subset of compounds that is of interest relates to compounds of formula I or a pharmaceutically acceptable salt or solvate thereof wherein:

ring A represents a phenyl or naphthyl group;

each $R^1$ and $R^2$ represents H or is selected from the group consisting of halo selected from fluoro and chloro; $SCH_3$; CN, $C_{1-6}$alkyl, $C_{2-4}$alkenyl and $C_{1-6}$alkoxy, the alkyl and alkenyl portions of $SCH_3$, $C_{1-6}$alkyl, $C_{2-4}$alkenyl and $C_{1-6}$alkoxy being optionally substituted with 1-3 fluoro atoms;

$R^3$ represents a member selected from the group consisting of: $CH_3$, ethyl, n-propyl, n-, s- and t-butyl, and allyl, and $R^4$ is selected from the group consisting of: H, Me, Et, n-propyl, n-butyl and benzyl. Within this aspect of the invention, all other variables are as originally defined with respect to formula I.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the list provided below.

Compounds of formula I may be used in combination with other drugs that are used in the treatment/prevention/suppression or amelioration of the diseases or conditions for which compounds of formula I are useful. Such other drugs may be administered, by a route and in an amount commonly used therefore, contemporaneously or sequentially with a compound of formula I. When a compound of formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I.

Examples of other active ingredients that may be combined with a compound of formula I for the treatment or prevention of type 2 diabetes and the other conditions described herein, either administered separately or in the same pharmaceutical compositions, include, but are not limited to:

(a) anti-obesity agents, such as (1) growth hormone secretagogues, growth hormone secretagogue receptor agonists/antagonists, such as NN703, hexarelin, MK-0677, SM-130686, CP424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. Nos. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-UV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046, 167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, (89) neuromedin U and analogs or derivatives thereof, (90) oxyntomodulin and analogs or derivatives thereof, (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; and (92) Qnexa; and (e) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]

benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl) [3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl] (4-cyanophenyl)methyl]azetidin-3-yl}-2-fluoro-2-methyl-propyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1, 2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b] pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro [7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1 (3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy] phenyl}-4-[(4-fluorobenzyl)oxy]pyridin-2(1H)-one, 4-[(4-fluorobenzyl)oxy]-1-{4-[(1-isopropylazetidin-3-yl)oxy] phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl) oxy]phenyl}pyridin-2(1H)-one, 4-[(5-chloropyridin-2-yl) methoxy]-1-{4-[(1-propylazetidin-3-yl)oxy] phenyl}pyridin-2(1H)-one, and 4-[(5-chloropyridin-2-yl) methoxy]-1-(4-{[(2S)-1-ethylazetidin-2-yl] methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2, 3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4 (3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4, 3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl] propoxy}phenyl)-4(3H)-quinazolinone, 2-methyl-3-(4-{3-[(3S)-3-methylpiperidin-1-yl]propoxy}phenyl)pyrido[2,3- d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof. Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof. Examples of other anti-obesity agents that can be employed in combination with a compound of formula I are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

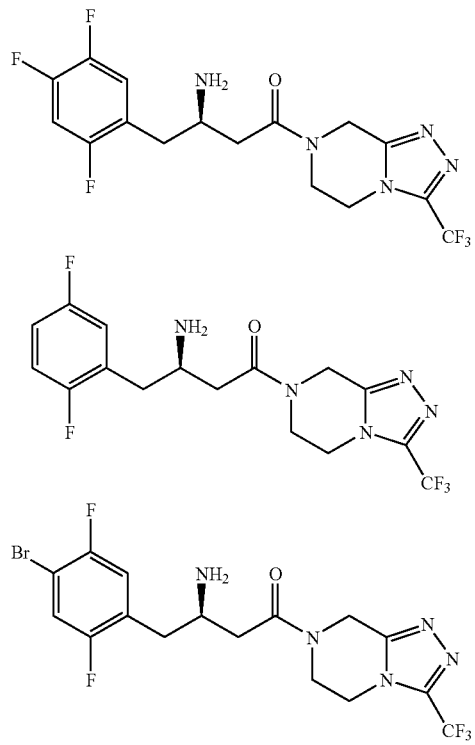

-continued

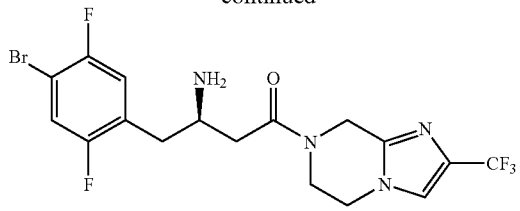

or a pharmaceutically acceptable salt or solvate thereof in combination with a pharmaceutically acceptable carrier.

Optical Isomers-Diastereomers-Geometric Isomers-Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg and 10 mg.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

The compounds of formula I can be synthesized in accordance with the general schemes provided below where $R^1$-$R^4$ and A are defined as above, taking into account the specific examples that are provided. Throughout the synthesis schemes, abbreviations are used with the following meanings unless otherwise indicated:

| | |
|---|---|
| aq = aqueous | BuLi, n-BuLi = n-butyllithium |
| Bu = butyl, t-Bu = t-butyl | Bn and Bnzl = benzyl |
| BOC, Boc = t-butyloxycarbonyl | CBZ, Cbz = Benzyloxycarbonyl |
| COD = cyclooctadiene | DCM = dichloromethane |
| CDI = carbonyl diimidazole | DIAD = diisopropylazodicarboxylate |
| DCC = Dicyclohexylcarbodiimide | DMAP = 4-Dimethylaminopyridine |
| DIEA = diisopropylethylamine | DMF = N,N-dimethylformamide |
| DMAC, DMA = dimethylacetamide | EtOH = ethanol |
| EDC = 1-ethyl-3-(3-dimethylaminopropyl)-carbodiimide | FAB-mass spectrum = Fast atom bombardment-mass spectroscopy |
| dppf = 1,1'-bis(diphenylphosphino)ferrocene | LCMS = liquid chromatography - mass spectroscopy |
| EtOAc = ethyl acetate | HPLC = High pressure liquid chromatography |
| eq. = equivalent(s) | LAH = Lithium aluminum hydride |
| HOAc = acetic acid | ESI = electrospray ionization |
| HOBT, HOBt = Hydroxybenztriazole | MeCN, $CH_3CN$ = acetonitrile |
| LHMDS = lithium | Pd/C = palladium on activated carbon |

| | |
|---|---|
| bis(trimethylsilyl)amide | |
| MeOH = methanol | TFA = Trifluoroacetic acid |
| Me = methyl | NMe$_2$ = dimethylamino |
| PBS = phosphate buffer saline | triflate = trifluoromethanesulonate |
| Ph = phenyl | IPA = isopropanol |
| THF = tetrahydrofuran | Py, Pyr = pyridyl |
| C$_6$H$_{11}$ = cyclohexyl | PyBOP = Benzotriazol-1-yloxytripyrrolidinophosphonium hexafluorophosphate |
| iPr = isopropyl | RT, rt = room temperature |
| 2,4-diClPh = 2,4-dichlorophenyl | Xantphos = 4,5-bis(diphenylphosphino)-9,9-dimethylxanthene |
| BINAP = 2,2'-bis(diphenylphosphino)-1,1'-binaphthalene | Pd$_2$dba$_3$ = tris(dibenzylideneacetone)dipalladium (0) |
| NaOtBu = sodium tert-butoxide | KOtBu = potassium tert-butoxide |
| Na$_2$SO$_4$ = sodium sulfate | MgSO$_4$ = magnesium sulfate |
| BOP = benzotriazol-1-yloxy-tris(dimethylamino)-phosphonium hexafluorophosphate | PMB = para methoxy benzyl |
| LDA = lithium diisopropylamide | KHMDS = potassium bis(trimethylsilyl)amide |
| NCS = N-chlorosuccinamide | DME = 1,2-dimethoxy ethane |

Compounds of the present invention may be prepared according to the methodology outlined in the following general synthetic schemes.

In one embodiment of the present invention, compound I may be prepared from the acid 1a by the sequence depicted in Scheme 1. The carboxylic acid intermediate 1a is coupled with commercially available beta alanine ester (either methyl, ethyl or t-butyl ester) using benzotriazol-1-yloxy-tris(dimethylamino)-phosphonium hexafluorophosphate (BOP) and a base, generally N,N-diisopropylethylamine (DIEA), in a solvent such as N,N-dimethylformamide (DMF) or acetonitrile at ambient temperature to yield compound 2a. Many peptide coupling conditions are known and may also be used. Saponification of beta alanine ester 2a (methyl, ethyl and t-butyl) to give compound I is achieved with a base such as aqueous lithium hydroxide (LiOH) or aqueous sodium hydroxide in a polar solvent such as tetrahydrofuran, methanol, ethanol or a mixture of similar solvents. In addition, compound 2a, containing a t-butyl beta alanine ester, can be converted to compound I using acid such as acetic acid or trifluoroacetic acid (TFA). The beta alanine moiety may also be incorporated at an earlier stage in the preparation of compound I (v.i.). This is most commonly done on allyl acid intermediate 1b to give the beta alanine ester intermediate 2b. The compounds are purified from unwanted side products by recrystallization, trituration, preparative thin layer chromatography, flash chromatography on silica gel as described by W. C. Still et al, *J. Org. Chem.* 1978 43, 2923, or HPLC. Compounds purified by reverse phase HPLC may be isolated as the corresponding salt. Purification of intermediates is achieved in the same manner.

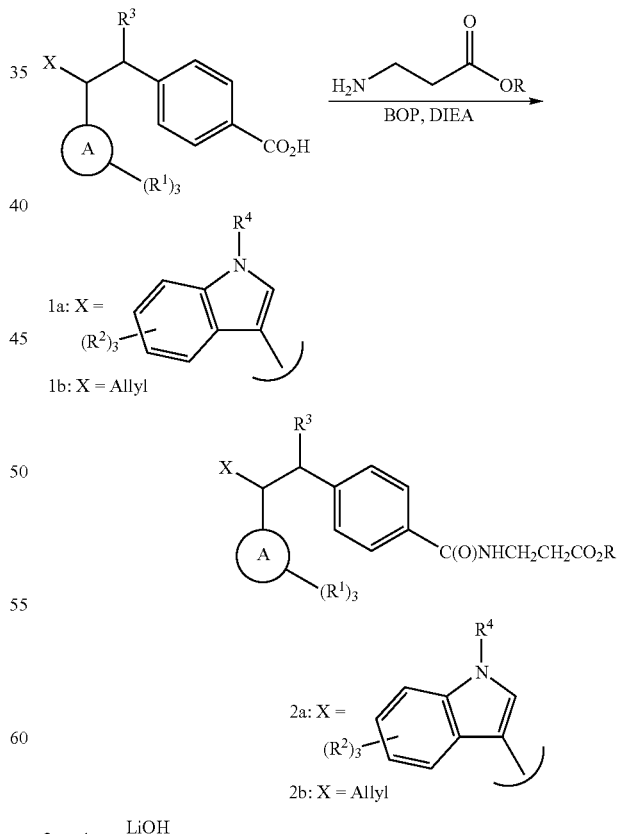

Scheme 1

-continued

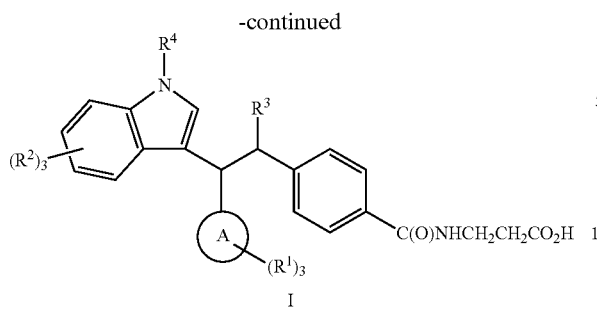

I

Conversion of 2b to compound I can be achieved by the sequence depicted in Scheme 2. Treatment of 2b with ozone gas in dichloromethane solvent at −78° C. followed by the addition of methylsulfide and triphenylphosphine affords the aldehyde 3. Alternatively, the same transformation can be achieved by dihydroxylation of the olefin moiety with a reagent such as osmium tetroxide followed by cleavage of the diol product with sodium periodate as described in *J. Org. Chem.* 1956, 21, 478. Treatment of aldehyde 3 with a phenyl hydrazine (or the corresponding phenyl hydrazine hydrogen chloride salt) and zinc chloride in acetic acid solvent at 80° C. (up to 120° C.) affords the indole 2a. The t-butyl beta alanine ester is cleaved under these conditions and gives compound I directly. Compound 2a possessing a methyl (or ethyl) beta alanine ester is then hydrolyzed with lithium hydroxide to give I. Phenyl hydrazines which are not commercially available may be prepared using methods familiar to those skilled in the art. One such method involves the diazotization of an aniline followed by reduction with a reagent such as tin chloride. Alternatively, phenyl hydrazines may be prepared by the palladium mediated coupling of a phenyl halide and benzophenone hydrazone as described in *J. Am. Chem. Soc.* 1998, 120(26), 6621.

Scheme 2

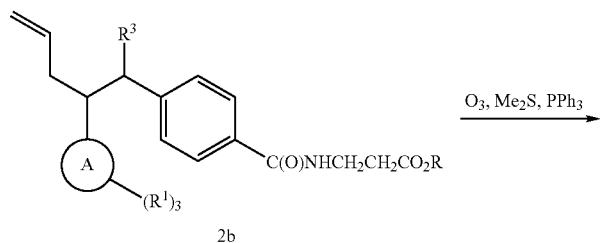

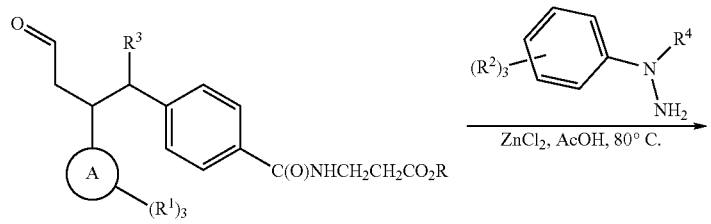

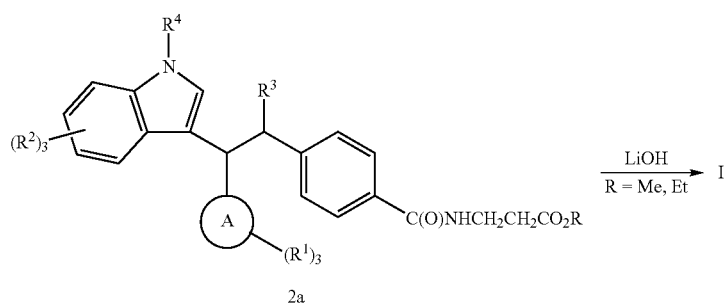

In another embodiment of the present invention, the compound I may be prepared from the indole intermediate 2c ($R^4$=H) by the sequence depicted in Scheme 3. Alkylation of the indole NH of intermediate 2c is achieved by treatment with a base such as potassium t-butoxide and an alkylating agent ($R^4$Br, $R^4$I, $R^4$OMs, etc) in an aprotic solvent such as dimethylacetamide. The beta alanine ester is then hydrolyzed as described previously to give I.

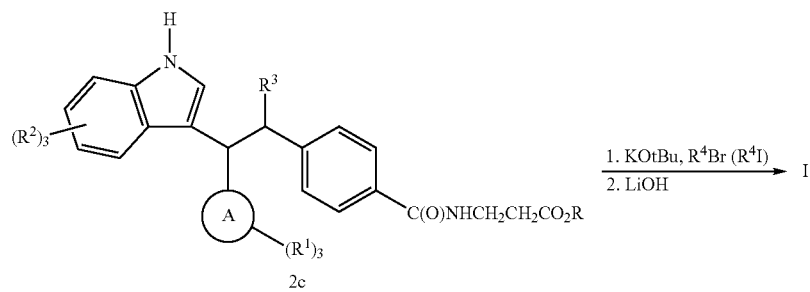

The following scheme summarizes the preparation of acid intermediate 1b which may be converted to compound I as described in the previous schemes. Palladium ($Pd_2dba_3$/BINAP) mediated coupling of 4-bromo t-buylbenzoate 4 and ketone 5 as described by Buchwald (*J. Am. Chem. Soc.* 1997, 119(45), 11108), gives 6. 4-Bromo t-buylbenzoate 4 is commercially available. Alternatively, it can be conveniently prepared by treatment of 4-bromobenzoyl chloride with potassium t-butoxide in THF. The ketone 5 may be commercially available or it can be prepared using methods familiar to those skilled in the art. One method is the oxidation of the corresponding alcohol. Alternatively, ketone 5 can be prepared by Grignard addition to a Weinreb amide as described in *Tet. Lett.* 1981, 22, 3815. The ketone 6 ($R^3$=H) can be alkylated using a base such as potassium t-butoxide and an alkylating agent ($R^3$Br, $R^3$I, etc) in THF solvent to give 6 ($R^3 \neq$H). Reduction of ketone 6 with $NaBH_4$ in methanol solvent gives the alcohol 7 (as a mixture of diastereomers>8:1). Treatment of alcohol 7 with allyltrimethylsilane and a Lewis acid such as $BF_3OEt_2$ in dichloromethane or dichloroethane solvent at 80° C. (up to 100° C.) affords the acid 1b. It will be recognized by those skilled in the art that this preparation gives racemic acid 1b. In addition there are two possible diastereomers of acid 1b (4 isomers total). The relative proportion is determined by the diastereoselectivity of the allyl addition (7 to 1b). Depending on the substituents A and $R^3$, the observed diasteroeselectivity under these reaction conditions ranges from a modest 1.2:1 to 8:1.

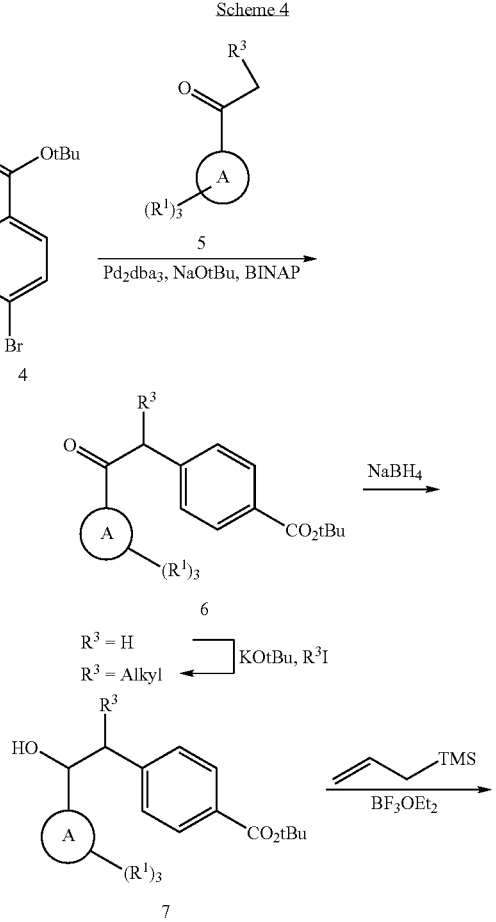

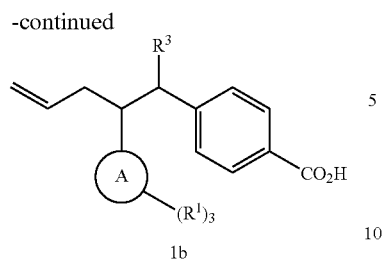

An alternative preparation of acid intermediate 1b is depicted in Scheme 5. 4-Bromophenylacetic acid 8 is coupled with (1R,2R)-(−)-pseudoephedrine, via the mixed anhydride generated with pivaloyl chloride and DIEA, to give amide 9. The amide 9 is alkylated with $R^3I$ using LDA and lithium chloride in THF at 0° C. to give 10. Reaction of amide 10 at 0° C. with aryl lithium 11, generated from the corresponding aryl bromide (or iodide) and butyllithium, gives the ketone 12. The transformation 8 to 12 is based on the chemistry described by Andrew G. Meyers (*J. Am. Chem. Soc.* 1997, 119, 6496) and from this precedent it can be expected that: 1) the alkylation of 9 is highly diastereoselective (>95%); 2) the ketone 12 is obtained in high enantiomeric purity (>90%); 3) the carbon bearing the $R^3$ substituent in ketone 12 has the R configuration (i.e. the $R^3$ bond is alpha as drawn in structure 12). The conversion of ketone 12 to the allyl intermediate 14 is carried out as described for 6 to 1b (Scheme 4). Carbonylation of 14 using $PdCl_2(PPh_3)_2$ catalyst, carbon monoxide gas and DIEA in n-butanol at 115° C. gives the n-butylester. Hydrolysis of the ester with aqueous lithium hydroxide as described previously gives the acid 1b. Alternatively, treatment of 14 with n-butyllithium and carbon dioxide gas directly affords the acid 1b. It will be recognized by those skilled in the art that this preparation, as in the preparation described in Scheme 4, affords acid 1b as a mixture of diastereomers. However, in this case the acid 1b will not be racemic.

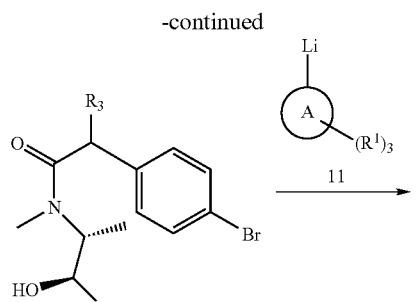

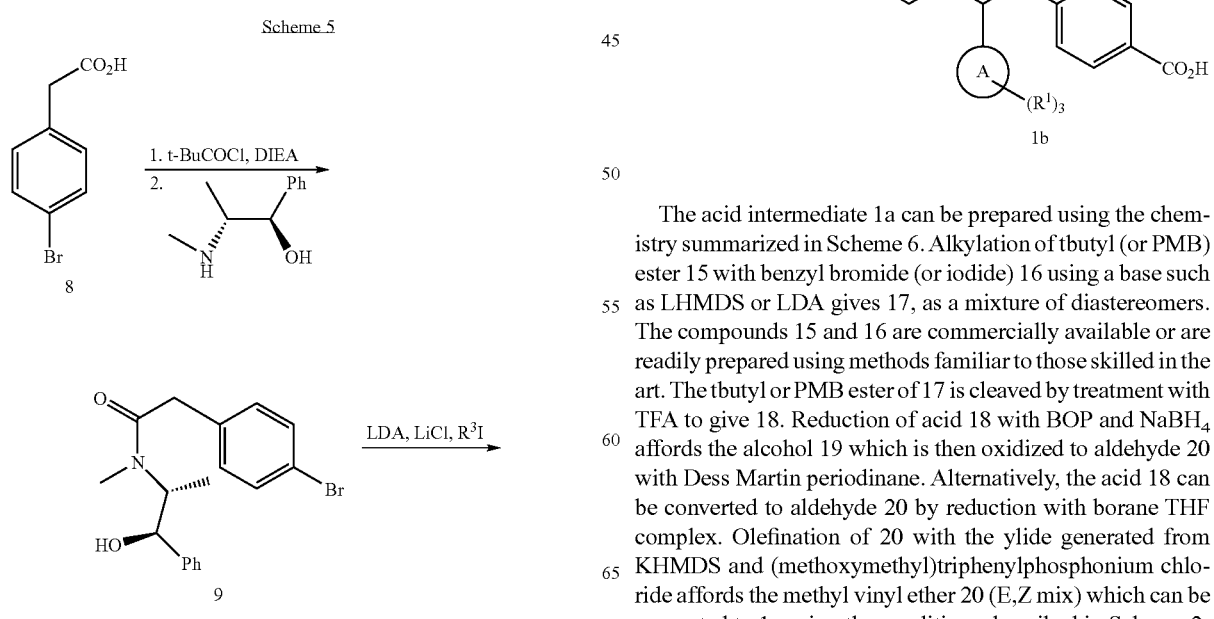

The acid intermediate 1a can be prepared using the chemistry summarized in Scheme 6. Alkylation of tbutyl (or PMB) ester 15 with benzyl bromide (or iodide) 16 using a base such as LHMDS or LDA gives 17, as a mixture of diastereomers. The compounds 15 and 16 are commercially available or are readily prepared using methods familiar to those skilled in the art. The tbutyl or PMB ester of 17 is cleaved by treatment with TFA to give 18. Reduction of acid 18 with BOP and $NaBH_4$ affords the alcohol 19 which is then oxidized to aldehyde 20 with Dess Martin periodinane. Alternatively, the acid 18 can be converted to aldehyde 20 by reduction with borane THF complex. Olefination of 20 with the ylide generated from KHMDS and (methoxymethyl)triphenylphosphonium chloride affords the methyl vinyl ether 20 (E,Z mix) which can be converted to 1a using the conditions described in Scheme 2.

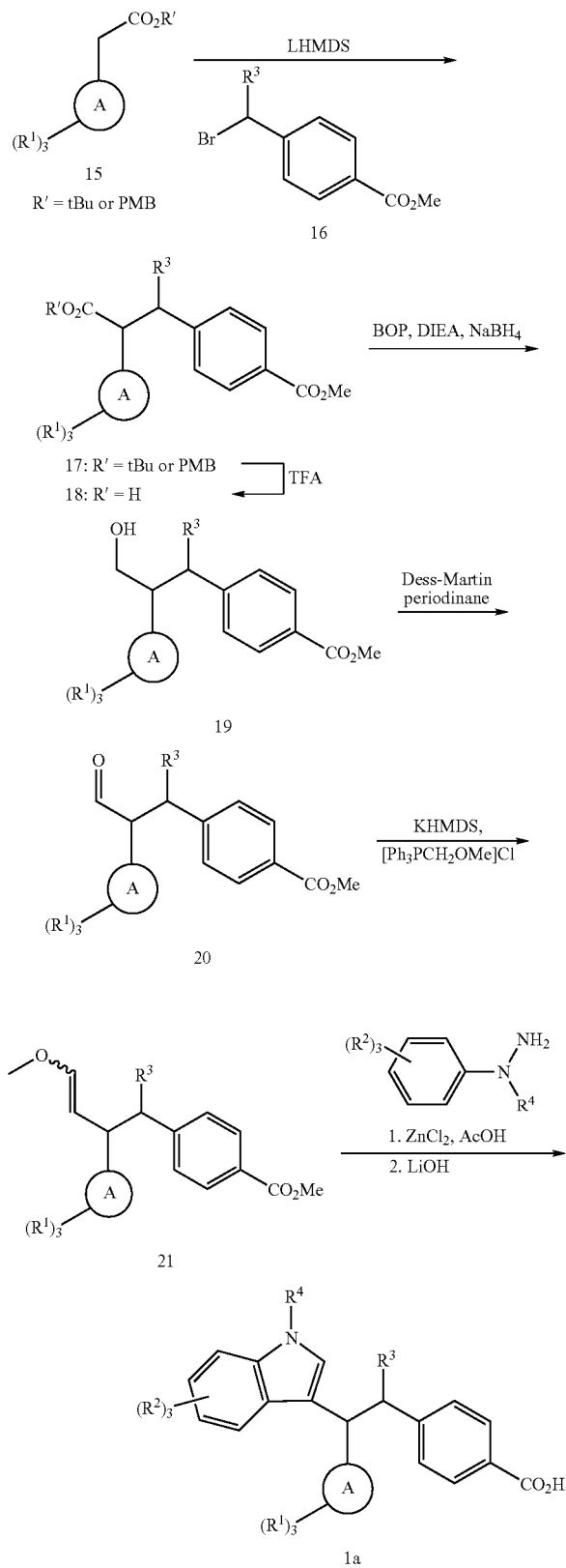

The $R^1$ substituent is typically present in the starting materials 5, 11 and 15. It can also be incorporated in advanced intermediates using methods familiar to those skilled in the art (see Scheme 7). One such method involves the Suzuki coupling of 22 with a vinyl boronic acid using $Pd(PPh_3)_4$ catalyst and potassium carbonate base. Coupling of 22 chloride with a vinyl boronic acid is achieved by using 1,1'-bis(di-t-butylphosphino)ferrocene palladium dichloride catalyst. The styrene product can be reduced with hydrogen gas and palladium/C catalyst to give 23. Another method involves the chlorination of methylether 24 with N-chlorosuccinamide to give 25.

is the slower (second) eluting. Separation of enantiomeric pairs (of the active diastereomer) is achieved by normal phase chromatography (i.e. EtOH/heptane or IPA/heptane eluent) or supercritical fluid chromatography ($CO_2$/MeOH eluent) using a chiral column available from Daicel®. Resolution is typically carried out on ester intermediate 2a using a CHIRALPAK® AD or CHIRALPAK® IA and EtOH (or IPA)/heptane eluent. In these cases the more active enantiomer is the slower (second) eluting enantiomer (for $R^4$=H only).

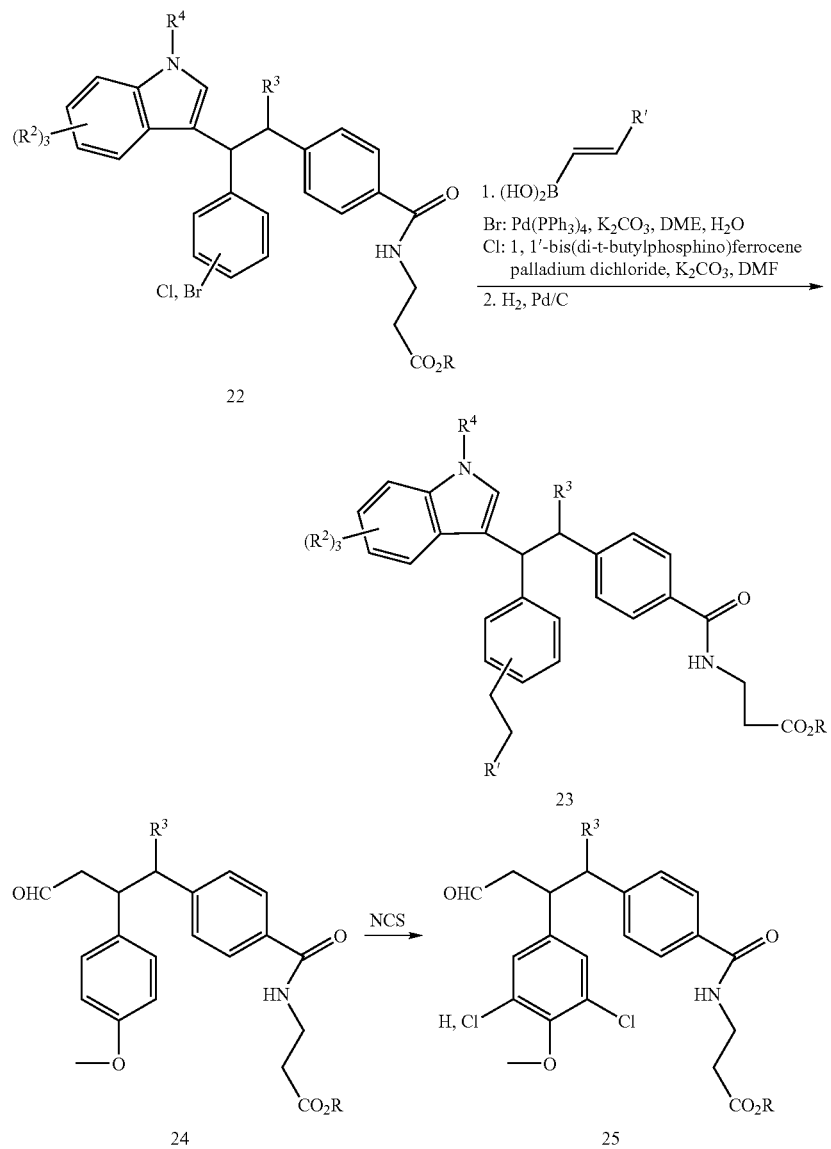

Scheme 7

Separation of diastereomers can be carried out at various stages in the preparation of I, however, it is typically carried out on the ester 2a using silica gel chromatography and EtOAc/hexane eluent or on compound I using reverse phase HPLC. In both cases the major, and more active diastereomer, Analytical HPLC Mass Spectrometry Conditions:

LC1: Column: Waters Xterra MS C-18, 3.5μ, 3.0×50 mm
  Temperature: 50° C.
  Eluent: 10:90 to 98:2 v/v acetonitrile/water+0.05% TFA over 3.75 min.

Flow Rate: 1.0 mL/min, Injection 10 μL

Detection: PDA, 200-600 nm

MS: mass range 150-750 amu; positive ion electrospray ionization

LC2: Column: Waters Xterra IS C-18, 3.5μ, 2.1×20 mm

Temperature: 50° C.

Eluent: 5:95 to 95:5 v/v acetonitrile/water+0.05% TFA over 0.75 min.

Flow Rate: 1.5 mL/min, Injection 5 μL

Detection: PDA, 200-600 nm

MS: mass range 150-750 amu; positive ion electrospray ionization

LC3: Column: Waters Xterra IS C-18, 3.5μ, 2.1×20 mm

Temperature: 50° C.

Eluent: 5:95 to 95:5 v/v acetonitrile/water+0.05% TFA over 3.00 min.

Flow Rate: 1.5 mL/min, Injection 5 μL

Detection: PDA, 200-600 nm

MS: mass range 150-750 amu; positive ion electrospray ionization

Analytical and Semi-Preparative Chiral HPLC Conditions:

Chiral LC1: Column: ChiralPak AD, 10μ, 4.6×250 mm

Temperature: ambient

Flow Rate: 0.75 mL/min

Detection: PDA, 254 nm

Injection Volume: 15 ul

General chiral semi-preparative conditions: 2 cm×25 cm column chiral column available from Daicel Chemical Industries, LTD, 9 ml/min isocratic EtOH or IPA/heptane eluent.

Preparative Reverse Phase HPLC (RP-HPLC) Conditions:

Column: Kromasil KR-10C8, 30×100 mm

Flow Rate: 50.0 mL/min

Or

Column: YMC-Pack Pro C18, 20×150 mm

Flow Rate: 20.0 mL/min

Eluent: acetonitrile/water+0.1% TFA

Gradient: 90 to 100:0 v/v acetonitrile/water+0.1% TFA over 10.0 min.

Temperature: ambient

Detection: PDA, 254 nm

Preparative thin layer chromatography (PTLC) was performed on 20×20 cm plates (500 μm thick silica gel) using a hexanes/ethyl acetate eluent. Silica gel chromatography was done on a Biotage Horizon flash chromatography system using a hexanes/ethyl acetate gradient.

The following examples are provided so that the invention might be more fully understood. They should not be construed as limiting the invention in any way.

INTERMEDIATE 1

Racemic 4-[2-(4-chlorophenyl)-1-propylpent-4-EN-1-YL]benzoic acid

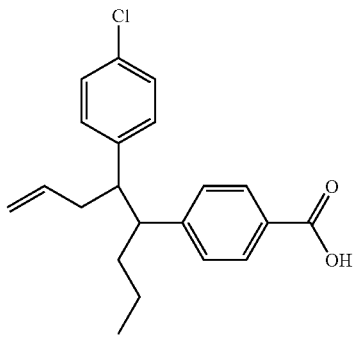

Step A. tert-Butyl 4-[2-(4-chlorophenyl)-2-oxoethyl]benzoate

A THF solution (200 ml) containing t-butyl 4-bromobenzoate (19.9 g, 77.6 mmol), 4-chloroacetophenone (10 g, 64.7 mmol), $Pd_2 dba_3$ (1.19 g, 1.29 mmol), BINAP (1.6 g, 2.58 mmol) and NaOtBu (8.7 g, 90.6 mmol) was refluxed under an argon atmosphere for approximately 5 hours. The solution was concentrated and then partitioned between EtOAc and water. The organic phase was washed with water, brine and dried over $Na_2SO_4$. The filtered solution was concentrated and the residue purified by silica gel chromatography using a hexanes/EtOAc gradient to give the title compound. $^1$H NMR (500 MHz, $CDCl_3$): δ 7.95 (d, J=8.5 Hz, 2H); 7.93 (d, J=8.7 Hz, 2H); 7.43 (d, J=8.3 Hz, 2H); 7.29 (d, J=8.2 Hz, 2H); 4.30 (s, 2H); 1.58 (s, 9H). LC1 4.01 min. (M-tBu+H)=275

Step B. tert-Butyl 4-[1-(4-chlorobenzoyl)butyl]benzoate

KOtBu (2.55 g, 22.7 mmol) was added to a cooled (ice bath) THF solution (40 ml) containing the intermediate from Step A (5.0 g, 15.15 mmol). After 10 minutes n-propyl iodide (3 ml, 30.3 mmol) was added dropwise. The ice bath was removed and the reaction was monitored by MS-HPLC analysis. The solution was then partitioned (<1 hour) between EtOAc and water. The organic phase was washed with water, brine and dried over $Na_2SO_4$. The filtered solution was concentrated and the residue purified by silica gel chromatography using a hexanes/EtOAc gradient to give the title compound. $^1$H NMR (400 MHz, $CDCl_3$): δ 7.90 (d, J=7.8 Hz, 2H); 7.84 (d, J=8.6 Hz, 2H); 7.33 (d, J=8.6 Hz, 2H); 7.31 (d, J=8.3 Hz, 2H); 4.51 (t, J=7.2 Hz, 1H); 2.18-2.08 (m, 1H); 1.84-1.68 (m, 1H); 1.54 (s, 9H); 1.38-1.18 (m, 2H); 0.90 (t, J=7.3 Hz, 3H). LC1 4.43 min. (M-tBu+H)=317

Step C. tert-Butyl 4-{1-[(4-chlorophenyl)(hydroxy)methyl]butyl}benzoate $NaBH_4$ (0.5 g, 13.21 mmol) was added in portions to a MeOH solution (40 ml) containing the intermediate from Step B (3.78 g, 10.16 mmol). After stirring for 1 hour the solution was concentrated and the residue partitioned between EtOAc and water. The organic phase was washed with water, brine and dried over $Na_2SO_4$. The filtered solution was concentrated and the residue purified by silica gel chromatography using a hexanes/EtOAc gradient to give the title compound as a >10:1 ratio of diastereomers. $^1$H NMR (400 MHz, CDCl$_3$): δ 7.93 (d, J=8.3 Hz, 2H); 7.28 (d, J=8.4 Hz, 2H); 7.23 (d, J=8.4 Hz, 2H); 7.18 (d, J=8.4 Hz, 2H); 4.73 (d, J=7.8 Hz, 1H); 2.89-2.83 (m, 1H); 1.58 (s, 9H); 1.57-1.56 (m, 1H); 1.41-1.33 (m, 1H); 1.09-0.91 (m, 2H); 0.72 (t, J=7.3 Hz, 3H). LC1 4.22 min. (M-tBu-OH+H)=301

Step D. 4-[2-(4-Chlorophenyl)-1-propylpent-4-en-1-yl]benzoic acid

A 1,2-dichloroethane (20 ml) solution containing the intermediate from Step C (1.81 g, 4.84 mmol), allyl trimethylsilane (6.2 ml, 38.7 mmol) and boron triflouride etherate (1.84 ml, 14.5 mmol) was heated at 80° C. for 1.5 hours. The solution was cooled to room temperature and methanol (10 ml) was slowly added. The solution was then concentrated and the residue partitioned between EtOAc and aqueous 1N HCl. The organic phase was washed with water, brine and dried over Na$_2$SO$_4$. The filtered solution was concentrated to give the title compound (as a ca 3:1 mixture of diastereomers) which was used without further purification. A portion was purified for spectral analysis. Data is for the major diastereomer $^1$H NMR (400 MHz, CDCl$_3$): δ 8.07 (d, J=8.3 Hz, 2H); 7.30 (d, J=5.7 Hz, 2H); 7.28 (d, J=5.4 Hz, 2H); 7.08 (d, J=8.3 Hz, 2H); 5.42-5.32 (m, 1H); 4.79-4.66 (m, 2H); 2.83-2.77 (m, 2H); 2.11-2.05 (m, 2H); 1.43-1.29 (m, 2H); 1.00-0.80 (m, 2H); 0.68 (t, J=7.3 Hz, 3H). LC1 4.08 min. (M+H)=343

NMR experiments (NOE) on advanced compounds (see EXAMPLE 1) derived from INTERMEDIATE 1 established the relative stereochemistry of the minor and major diastereomers of INTERMEDIATE 1 as:

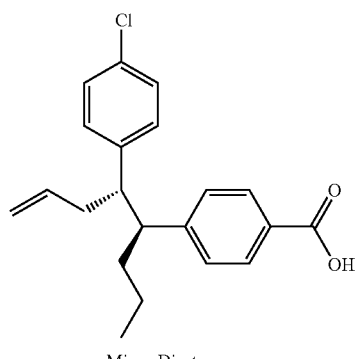

Minor Diastereomer

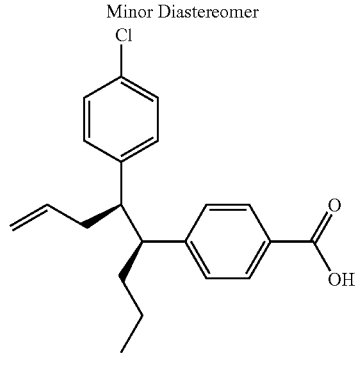

Major Diastereomer

INTERMEDIATE 2

4-[(1S,2R)-2-(4-chlorophenyl)-1-propylpent-4-en-1-yl]benzoic acid

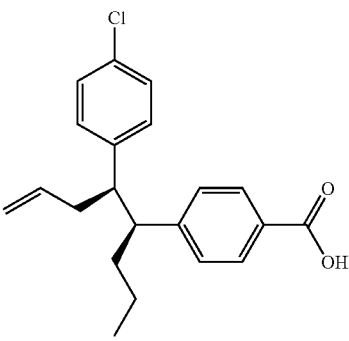

Step A. 2-(4-Bromophenyl)-N-[(1R,2R)-2-hydroxy-1-methyl-2-phenylethyl]-N-methylacetamide Pivaloyl chloride (7.8 ml, 63.3 mmol) was added dropwise to a DCM/THF solution (100 ml/20 ml) containing 4-bromophenylacetic acid (13.59 g, 63.2 mmol). DIEA (11.0 ml, 63.1 mmol) was then added dropwise (exotherm). After stirring at room temperature for 1 hour the solution was poured slowly into a DCM/THF solution (100 ml/20 ml) containing (1R,2R)-(−)-pseudoephedrine (10.5 g, 63.5 mmol) and DIEA (11.0 ml, 63.1 mmol). After stirring overnight at room temperature the solution was concentrated and the residue partitioned between EtOAc and water. The organic phase was washed with aqueous 1N NaOH (2×), aqueous 1N HCl (3×), brine and dried over MgSO$_4$. The solution was filtered and concentrated. The oil residue was diluted with 100 ml of toluene and concentrated. The residue was then dissolved in ethyl ether and triturated with hexanes to give the title compound as a white solid. The compound is a 3:1 mixture of amide rotational isomers by proton NMR: $^1$H NMR (400 MHz, asterisk denotes minor rotamer, CDCl$_3$): δ 7.42 (d, J=8.3 Hz, 2H); 7.39-7.27 (m, 5H); 7.11*(d, J=8.4 Hz, 2H); 7.04 (d, J=8.3 Hz, 2H); 4.64-4.42 (m, 1H); 4.07-3.94 (m, 1H); 3.82-3.70 (m, 1H); 2.94*(s, 3H); 3.63 (s, 2H); 2.82 (s, 3H); 1.12 (d, J=7.0 Hz, 3H); 0.86*(d, 3H, J=7.0 Hz). LC1 3.23 min. (M+H)=362

Step B. 2-(4-Bromophenyl)-N-[(1R,2R)-2-hydroxy-1-methyl-2-phenylethyl]-N-methylpentanamide THF (40 ml) was added to dry lithium chloride (8 g, 189 mmol) and diisopropyl amine (9.2 ml, 65.6 mmol) under an argon atmosphere. The suspension was cooled to −78° C. and n-BuLi (1.6M in hexanes, 37.9 ml, 60.6 mmol) was added dropwise. After stirring for 5 minutes the solution was warmed to 0° C. After 5 minutes the solution was cooled to −78° C. and a THF solution (45 ml) containing the intermediate from Step A (10.56 g, 29.15 mmol) was added dropwise. The solution was then stirred at −78° C. for 1 hour and then warmed to 0° C. After 15 minutes n-propyl iodide (4.3 ml, 44.1 mmol) was added dropwise. The solution was stirred at 0° C. for approximately 2 hours. To the reaction mixture was added saturated aqueous NH$_4$Cl and EtOAc. The phases were separated and the aqueous phase extracted with EtOAc. The combined organic phases were dried over Na$_2$SO$_4$, filtered and concentrated. The oil residue was dissolved in ethyl ether/hexanes (4/6) and filtered through a short plug of silica gel. The filtered solution was concentrated to give the title compound. The compound is a 3:1 mixture of amide rotational isomers by proton NMR: $^1$H NMR (400 MHz, asterisk denotes minor rotamer, CDCl$_3$): δ 7.42 (d, J=8.4 Hz, 2H); 7.41-7.27 (m, 5H); 7.08 (d, J=8.4 Hz, 2H); 4.56 (q, J=6.7 Hz, 1H); 4.42 (br s 1H); 4.17-4.01*(m, 1H); 3.85*(t, J=7.1 Hz, 1H); 3.55 (t, J=7.2 Hz, 1H); 3.00*(s, 3H); 2.72 (s, 3H); 2.07-1.92 (m, 1H); 1.69-1.58 (m, 1H); 1.33-1.13 (m, 2H); 1.11 (d, J=7.0 Hz, 3H); 0.88 (t, J7.3 Hz, 3H): 0.58*(d, J=6.9 Hz, 3H). LC1 3.76 min. (M+H)=404

Step C. 2-(4-Bromophenyl)-1-(4-chlorophenyl)pentan-1-one n-Butyl lithium (1.0M in THF, 59 ml, 94.5 mmol) was added dropwise to a −78° C. THF solution (200 ml) containing 4-chloro bromobenzene (22.63 g, 118.2 mmol) under an argon atmosphere. After 10 minutes a THF solution (30 ml) of the intermediate from Step B (15.88 g, 39.4 mmol) was added dropwise. The solution was warmed to 0° C. and stirred for 30 minutes. Diisopropylamine (5.6 ml, 39.4 mmol) was then added dropwise. After 10 minutes the reaction solution was diluted with 200 ml of AcOH/ethyl ether (1/10 by volume). The mixture was partitioned between EtOAc and saturated aqueous NaHCO$_3$ (foaming). The organic phase was washed with saturated aqueous NaHCO$_3$, water, brine and dried over Na$_2$SO$_4$. The filtered solution was concentrated and the residue purified by silica gel chromatography using hexanes/EtOAc gradient to give the title compound. $^1$H NMR (500 MHz, CDCl$_3$): δ 7.86 (d, 2H, J=8.5 Hz); 7.41 (d, 2H, J=8.5 Hz); 7.37 (d, 2H, J=8.5 Hz); 7.15 (d, 2H, J=8.5 Hz); 4.45 (t, J=7.3 Hz, 1H); 2.15-2.07 (m, 1H); 1.81-1.73 (m, 1H); 1.33-1.19 (m, 2H); 0.91 (t, J=7.4 Hz, 3H). LC1 4.25 min. Not ionized

Step D. 2-(4-Bromophenyl)-1-(4-chlorophenyl)pentan-1-ol

Sodium borohydride (917 mg, 24.25 mmol) was added to a MeOH solution (25 ml) containing the intermediate from Step C (6.53 g, 18.66 mol). After stirring for 1 hour at room temperature the solution was concentrated and the residue partitioned between water and EtOAc. The organic phase was washed with water, brine and dried over Na$_2$SO$_4$. The filtered solution was concentrated to give the title compound as an 8:1 mixture of diastereomers which was used in the next step without further purification. $^1$H NMR for major diastereomer (500 MHz, CDCl$_3$): δ 7.44 (d, J=8.1 Hz, 2H); 7.30 (d, J=8.5 Hz, 2H); 7.19 (d, J=8.5 Hz, 2H); 7.07 (d, J=8.1 Hz, 2H); 4.71-4.68 (m, 1H); 2.81-2.74 (m, 1H); 1.56-1.48 (m, 1H); 1.42-1.32 (m, 1H); 1.12-0.95 (m, 2H); 0.75 (t, J=7.3 Hz, 3H). LC1 4.00 min. (M−OH)=335

Step E. 1-Bromo-4-[2-(4-chlorophenyl)-1-propylpent-4-en-1-yl]benzene

The title compound was prepared from the intermediate from Step D using the conditions described in INTERMEDIATE 1, Step D. The title compound is obtained as a 2.1:1 mixture of diastereomers. $^1$H NMR for major diastereomer (500 MHz, CDCl$_3$): δ 7.44 (d, J=8.5 Hz, 2H); 7.28 (d, J=8.3 Hz, 2H); 7.05 (d, J=8.2 Hz, 2H); 7.02 (d, J=8.4 Hz, 2H); 5.46-5.35 (m, 1H); 4.82-4.71 (m, 2H); 2.77-2.62 (m, 2H); 2.14-2.02 (m, 2H); 1.35-1.25 (m, 2H); 1.05-0.89 (m, 2H); 0.67 (t, J=7.3 Hz, 3H). LC1 4.66 min. Not ionized

Step F. n-Butyl 4-[2-(4-chlorophenyl)-1-propylpent-4-en-1-yl]benzoate

An n-butanol solution (5 ml) containing the intermediate from Step E (108 mg, 0.286 mmol), DIEA (0.15 ml, 0.86 mmol) and PdCl$_2$(PPh$_3$)$_2$ (376 mg, 0.06 mmol) was heated at 115° C. under a carbon monoxide atmosphere (balloon). After 1 hour the solution was cooled and concentrated. The residue was dissolved in EtOAc and filtered. The residue was used without purification in the next step. A portion was purified for spectral analysis. $^1$H NMR for major diastereomer (500 MHz, CDCl$_3$): δ 8.00 (d, J=8.3 Hz, 2H); 7.28 (d, J=8.4 Hz, 2H); 7.23 (d, J8.3 Hz, 2H): 7.07 (d J=8.4 Hz, 2H); 5.42-5.31 (m, 1H); 4.77-4.66 (m, 2H); 4.33 (t, J=6.6 Hz, 2H); 2.80-2.75 (m, 2H); 2.10-2.06 (m, 2H); 1.81-1.68 (m, 2H); 1.41-1.24 (m, 4H); 0.99 (t, J=7.4 Hz, 3H); 0.98-0.86 (m, 4H); 0.67 (t, J=7.3 Hz, 3H). LC1 4.73 min. (M+H)=399

Step G. 4-[(1S,2R)-2-(4-chlorophenyl)-1-propylpent-4-en-1-yl]benzoic acid

A THF/MeOH/water (8 ml/8 ml/3 ml) solution containing the intermediate from Step F (790 mg, 1.98 mmol) and lithium hydroxide monohydrate (406 mg, 9.90 mmol) was stirred overnight at room temperature. The solution was concentrated and the nonvolatile portion was partitioned between aqueous 2N hydrochloric acid and EtOAc. The organic phase was dried over Na$_2$SO$_4$, filtered and concentrated to give the title compound. $^1$H NMR (500 MHz, DMSO-d$_6$): δ 7.90 (d, J=8.2 Hz, 2H); 7.39 (d, J=8.5 Hz, 2H); 7.36 (d, J=8.5 Hz, 2H); 7.26 (d, J=8.4 Hz, 2H); 5.36-5.26 (m, 1H); 4.71-4.60 (m, 2H); 2.94-2.84 (m, 2H); 2.13-2.07 (m, 1H); 1.95-1.87 (m, 1H); 1.42-1.34 (m, 1H); 1.19-1.11 (m, 1H); 0.85-0.77 (m, 2H); 0.60 (t, J=7.3 Hz, 3H). LC3 2.57 min (M+H) 343

Alternatively, the title compound can be prepared from the intermediate from Step E. A pentane solution of t-BuLi (1.7M, 3.08 ml, 5.23 mmol) was added dropwise to a THF solution (20.1 ml) of the intermediate from Step E (760 mg, 2.01 mmol) cooled to −78° C. After 5 minutes, CO$_2$ gas was bubbled for a half minute through the solution. The cooling bath was removed and the solution was warmed to room temperature. The solution was then diluted with aqueous 2N HCl and extracted with EtOAc (2×). The combined organic phases were dried over Na$_2$SO$_4$, filtered and concentrated to give the title compound.

The absolute stereochemistry of the minor and major diastereomers of INTERMEDIATE 2 is shown below. This assignment is based on the known configuration of the n-propyl substituted carbon, which is derived from the (−)-pseudoephedrine, and NMR experiments (NOE) on advanced compounds (see EXAMPLE 1) derived from INTERMEDIATE 2.

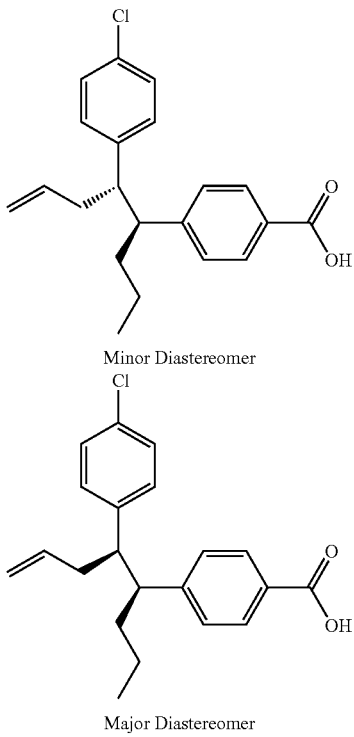

Minor Diastereomer

Major Diastereomer

EXAMPLE 1

N-(4-{1-[(4-chlorophenyl)(5,7-dichloro-1H-indol-3-yl)methyl]butyl}benzoyl)-β-alanine

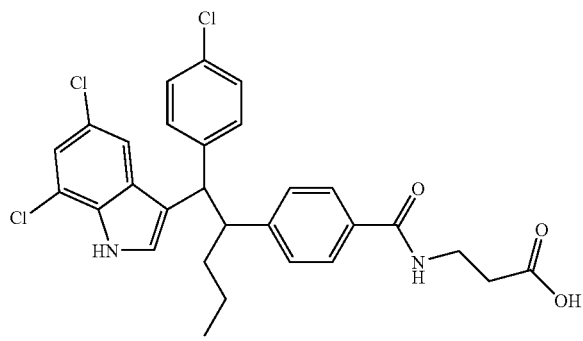

Step A. Methyl N-{4-[2-(4-chlorophenyl)-1-propyl-pent-4-en-1-yl]benzoyl}-β-alaninate A DMF solution (20 ml) containing INTERMEDIATE 1 (1.66 g, 4.84 mmol), methyl β-alaninate hydrochloride (1.01 g, 7.26 mmol), DIEA (4.3 ml, 24.2 mmol) and BOP (3.21 g, 7.26 mmol) was stirred at room temperature for 1.5 hours. The solution was diluted with EtOAc and washed with water, brine and dried over $Na_2SO_4$. The filtered solution was concentrated and the residue purified by silica gel chromatography using a hexanes/EtOAc gradient to give the title compound. $^1$H NMR for the major diastereomer (500 MHz, $CDCl_3$): δ 7.72 (d, J=8.2 Hz, 2H); 7.28 (d, J=8.3 Hz, 2H); 7.22 (d, J=8.2 Hz); 7.07 (d, J=8.4 Hz, 2H); 6.85-6.81 (m, 1H); 5.41-5.31 (m, 1H); 4.77-4.66 (m, 2H); 3.75-3.70 (m, 2H); 3.73 (s, 3H); 2.81-2.72 (m, 2H); 2.67 (t, J=5.9 Hz, 2H); 2.10-2.05 (m, 2H); 1.40-1.29 (m, 2H); 0.98-0.85 (m, 2H); 0.66 (t, J=7.3 Hz, 3H). LC1 4.03 min. (M+H)=428

Step B. Methyl N-{4-[2-(4-chlorophenyl)-4-oxo-1-propylbutyl]benzoyl}-β-alaninate Ozone was purged through a chilled (−78° C.) DCM solution (20 ml) containing the intermediate from Step A (1.59 g, 3.72 mmol). The ozone purge was maintained until an excess of ozone was observed (blue color, <10 minutes). The solution was then purged with nitrogen to dissipate the excess ozone. To the solution was added dimethylsulfide (1 ml) followed by triphenylphosphine (977 mg, 3.72 mmol). The solution was warmed to room temperature and stirred for approximately 2 hours. The solution was concentrated and the residue purified by silica gel chromatography using a hexanes/EtOAc gradient to give the title compound. $^1$H NMR for the major diastereomer (500 MHz, $CDCl_3$): δ 9.34 (s, 1H); 7.73 (d, J=8.2 Hz, 2H); 7.30 (d, J=8.3 Hz, 2H); 7.23 (d, J=8.0 Hz, 2H); 7.16 (d, J=8.4 Hz, 2H); 6.87-6.83 (broad s, 1H); 3.72 (s, 3H); 3.75-3.71 (m, 2H); 3.36-3.31 (m, 1H); 2.80-2.72 (m, 1H); 2.69-2.63 (m, 2H); 2.61-2.52 (m, 1H); 2.38 (dd, J=3.9, 17.1 Hz, 1H); 1.45-1.28 (m, 2H); 1.06-0.78 (m, 2H); 0.66 (t, J=7.3 Hz, 3H). LC1 3.55 min. (M+H)=430

Step C. Methyl N-(4-{1-[(4-chlorophenyl)(5,7-dichloro-1H-indol-3-yl)methyl]butyl}benzoyl)-β-alaninate An acetic acid solution (5 ml) containing the intermediate from Step B (200 mg, 0.47 mmol), 2,4-dichlorophenyl hydrazine hydrochloride (120 mg, 0.56 mmol) and $ZnCl_2$ (2.29M in AcOH, 0.61 ml, 1.4 mmol) was heated at 80° C. for 30 minutes. The solution was concentrated and the residue dissolved in EtOAc. The EtOAc solution was washed with water, brine and dried over $Na_2SO_4$. The filtered solution was concentrated and the residue purified by silica gel chromatography using a hexanes/EtOAc gradient to give the title compound as a mixture of diastereomers. The mixture was purified further using reverse phase HPLC. The major (and more active) diastereomer, which is also the slower (second) eluting on HPLC, was resolved on a Chiralpak AD-H column (2 cm×25 cm) eluting with 10% EtOH/Heptane at 9 ml/min.

Data for the faster eluting enantiomer: Chiral LC1: (1% to 15% EtOH/heptane over 25 min, 15% EtOH/heptane isocratic>25 min) retention time=25.34 minutes. $^1$H NMR (400 MHz, $CD_3CN$): δ 9.36 (s, 1H); 7.54 (d, J=8.3 Hz); 7.48 (d, J=8.3 Hz, 2H); 7.47 (s, 1H); 7.37 (d, J=8.3 Hz, 2H); 7.31 (d, J=8.3 Hz, 2H); 7.29 (d, J=2.4 Hz, 1H); 7.07 (d, J=1.6 Hz, 1H); 7.02-6.95 (m, 1H); 4.49 (d, J=11.6 Hz, 1H); 3.60 (s, 3H); 3.58-3.47 (m, 3H); 2.52 (t, J=6.9 Hz, 2H); 1.52-1.35 (m, 2H); 1.01-0.90 (m, 2H); 0.69 (t, J=7.4 Hz, 3H). LC1 4.16 min. (M+H)=571

Data for the slower eluting enantiomer (more active): Chiral LC1: (1% to 15% EtOH/heptane over 25 min, 15% EtOH/heptane isocratic>25 min) retention time=28.46 minutes. $^1$H NMR (400 MHz, $CD_3CN$): δ 9.37 (s, 1H); 7.54 (d, J=8.3 Hz); 7.48 (d, J=8.3 Hz, 2H); 7.47 (s, 1H); 7.37 (d, J=8.3 Hz, 2H); 7.31 (d, J=8.3 Hz, 2H); 7.29 (d, J=2.6 Hz, 1H); 7.07 (d, J=1.7 Hz, 1H); 7.02-6.95 (m, 1H); 4.49 (d, J=11.7 Hz, 1H); 3.60 (s, 3H); 3.58-3.47 (m, 3H); 2.53 (t, J=6.9 Hz, 2H); 1.52-1.35 (m, 2H); 1.01-0.90 (m, 2H); 0.69 (t, J=7.4 Hz, 3H). LC1 4.16 min. (M+H)=571

Step D. N-(4-{1-[(4-Chlorophenyl)(5,7-dichloro-1H-indol-3-yl)methyl]butyl}benzoyl)-β-alanine The isomers obtained in Step C were hydrolyzed using the conditions described in INTERMEDIATE 2, Step G. The crude hydrolysis was purified by HPLC to give the title compounds. Data for the minor diastereomer (racemic): $^1$H NMR (400 MHz, CD$_3$CN): δ 9.66 (s, 1H); 7.71 (d, J=1.6 Hz, 1H); 7.56 (d, J=8.3 Hz, 2H); 7.51 (d, J=2.6 Hz, 1H); 7.29 (d, J=8.3 Hz, 2H); 7.22-7.18 (m, 3H); 7.08 (broad s, 1H); 7.02 (d, J=8.5 Hz, 2H); 4.46 (d, J=11.6 Hz, 1H); 3.62-3.50 (m, 3H); 2.56 (t, J=6.7 Hz, 2H); 1.78-1.68 (m, 1H); 1.62-1.52 (m, 1H); 1.09-0.91 (m, 2H); 0.71 (t, J=7.3 Hz, 3H). LC1 3.87 min. (M+H) =557.

Data for the Major Diastereomer, Faster Eluting Enantiomer:

$^1$H NMR (500 MHz, CD$_3$CN): δ 9.38 (s, 1H); 7.55 (d, J=8.3 Hz, 2H); 7.48 (d, J=8.3 Hz, 2H); 7.47-7.46 (m, 1H); 7.37 (d, J=8.3 Hz, 2H); 7.31 (d, J=8.4 Hz, 2H); 7.28 (d, J=2.5 Hz, 1H); 7.06 (d, J=1.8 Hz, 1H); 7.05 (broasd s, 1H); 4.50 (d, J=11.6 Hz, 1H); 3.55-3.47 (m, 3H); 2.52 (t, J=6.6 Hz, 2H); 1.49-1.38 (m, 2H); 0.99-0.91 (m, 2H); 0.69 (t, J=7.3 Hz, 3H). LC1 4.03 min. (M+H)=557. [α]=+118.2° (589 nm, EtOH)

Data for the Major Diastereomer, Slower Eluting Enantiomer (More Active):

$^1$H NMR (500 MHz, CD$_3$CN): δ 9.36 (s, 1H); 7.56 (d, J=8.3 Hz, 2H); 7.49 (d, J=8.7 Hz, 2H); 7.49-7.47 (m, 1H); 7.38 (d, J=8.3 Hz, 2H); 7.33 (d, J=8.5 Hz, 2H); 7.29 (d, J=2.5 Hz, 1H); 7.08 (d, J=1.7 Hz, 1H); 7.03 (broad s, 1H); 4.51 (d, J=11.7 Hz, 1H); 3.57-3.53 (m, 1H); 3.52-3.48 (m, 2H); 2.53 (t, J=6.7 Hz, 2H); 1.51-1.39 (m, 2H); 1.01-0.93 (m, 2H); 0.70 (t, J=7.3 Hz, 3H). LC1 4.03 min. (M+H)=557. [α]=−105.7 2° (589 nm, EtOH)

The relative stereochemistry of the two diastereomers of EXAMPLE 1 is shown in the figure below. The stereochemistry assignment is based on the observed Nuclear Overhauser Effect (NOE, represented by an asterisk) and a low energy conformational model of the two diastereomers. EXAMPLE 1 was also prepared as described above using the enantiopure INTERMEDIATE 2. The obtained material (major diastereomer) correlates with the slower eluting enantiomer. Based on the known configuration of the n-propyl substituted carbon, which is derived from the (−)-pseudoephedrine in INTERMEDIATE 2, the structure drawn for Diastereomer B also indicates the absolute stereochemistry of the slower eluting enantiomer.

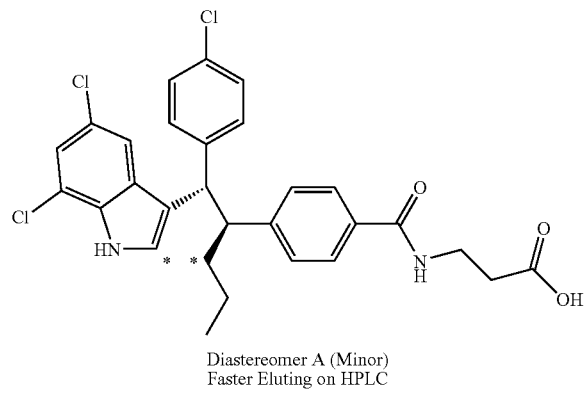

Diastereomer A (Minor)
Faster Eluting on HPLC

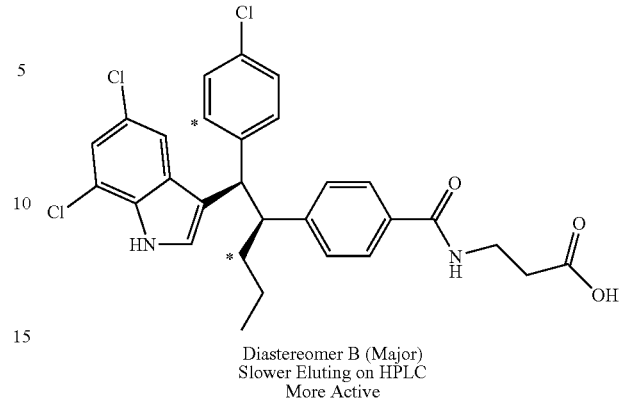

Diastereomer B (Major)
Slower Eluting on HPLC
More Active

EXAMPLE 2

N-(4-{(1S)-1-[(R)-(4-chlorophenyl)(7-fluoro-5-methyl-1H-indol-3-yl)methyl]butyl}benzoyl)-β-alanine

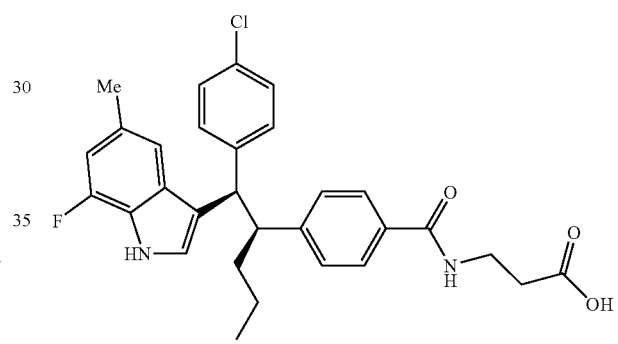

Step A. Methyl N-(4-{(1S)-1-[(R)-(4-chlorophenyl)(7-fluoro-5-methyl-1H-indol-3-yl)methyl]butyl}benzoyl)-β-alaninate An acetic acid solution (10 ml) of methyl N-{4-[2-(4-chlorophenyl)-4-oxo-1-propylbutyl]benzoyl}-β-alaninate, prepared from INTERMEDIATE 2 as described in EXAMPLE 1, (757 mg, 1.76 mmol), ZnCl$_2$ (3.1M in AcOH, 1.7 ml, 5.27 mol) and 2-fluoro-4-methylphenylhydrazine hydrochloride (374 mg, 2.1 mmol) were heated at 80° C. for 45 minutes. The solution was concentrated and the residue partitioned between EtOAc and water. The organic phase was washed with water (2×), brine (2×) and dried over Na$_2$SO$_4$. The solution was filtered, concentrated and the residue purified by silica gel chromatography using a hexanes/ethyl acetate gradient to give the title compound. Data for the major diastereomer: $^1$H NMR (500 MHz, CD3CN): δ 9.11 (s, 1H); 7.54 (d, J=8.2 Hz, 2H); 7.48 (d, J=8.5 Hz, 2H); 7.38 (d, J=8.2 Hz, 2H); 7.30 (d, J=8.4 Hz, 2H); 7.15 (d, J=2.5 Hz, 1H); 7.11 (s, 1H); 7.02-6.97 (m, 1H); 6.59 (d, J=12.3 Hz, 1H); 4.49 (d, J=11.6 Hz, 1H); 3.60 (s, 3H); 3.56-3.48 (m, 3H); 2.52 (t, J=6.8 Hz, 2H); 2.32 (s, 3H); 1.49-1.35 (m, 2H); 1.04-0.90 (m, 2H); 0.69 (t, J=7.4 Hz, 3H). LC1=3.94 min. (M+H)=535. Chiral LC1 (1% to 15% EtOH/heptane over 25 min, 15% EtOH/heptane isocratic>25 min) retention time=28.38 minutes. The material also contains ca 2% by area of the enantiomer. Chiral LC1 (1% to 15% EtOH/heptane over 25 min, 15% EtOH/heptane isocratic>25 min) retention time=26.88 minutes.

Step B. N-(4-{(1S)-1-[(R)-(4-Chlorophenyl)(7-fluoro-5-methyl-1H-indol-3-yl)methyl]butyl}benzoyl)-β-alanine The isomers obtained in Step A were hydrolyzed using the conditions described in INTERMEDIATE 2, Step G. The crude hydrolysis was purified by HPLC to give the title compounds. Data for the minor diastereomer: $^1$H NMR (400 MHz, CD$_3$CN): δ 9.39 (s, 1H); 7.56 (d, J=8.0 Hz, 2H); 7.37 (d, J=2.4 Hz, 1H); 7.33 (s, 1H); 7.29 (d, J=8.0 Hz, 2H); 7.20 (d, J=8.4 Hz); 7.07 (broad s, 1H); 7.01 (d, J=8.4 Hz, 2H); 6.72 (d, J=12.4 Hz, 1H); 4.45 (d, J=11.6 Hz, 1H); 3.65-3.55 (m, 1H); 3.52 (q, J=6.4 Hz, 2H); 2.55 (t, J=6.8 Hz, 2H); 2.40 (s, 3H); 1.84-1.73 (m, 1H); 1.63-1.52 (m, 1H); 1.10-0.93 (m, 2H); 0.71 (t, J=7.2 Hz, 3H). LC1=3.66 min. (M+H)=521

Data for the major diastereomer: $^1$H NMR (500 MHz, CD$_3$CN): δ 9.11 (s, 1H); 7.56 (d, J=8.2 Hz, 2H); 7.49 (d, J=8.4 Hz, 2H); 7.39 (d, J=8.2 Hz, 2H); 7.31 (d, J=8.4 Hz, 2H); 7.16 (d, J=2.4 Hz, 1H); 7.12 (s, 1H); 7.04 (s, 1H); 6.60 (d, J=12.2 Hz, 1H); 4.50 (d, J=11.6 Hz, 1H); 3.58-3.53 (m, 1H); 3.50 (q, J=6.4 Hz, 2H); 2.53 (t, J=6.6 Hz, 2H); 2.33 (s, 3H); 1.51-1.37 (m, 2H); 0.99-0.92 (m, 2H); 0.70 (t, J=7.3 Hz, 3H). LCMS1 3.83 min. (M+H)=521. [α]=−126.6° (589 nm, EtOH)

The compounds in TABLE 1 were prepared using the chemistry described in EXAMPLES 1 and 2. The data for the racemic compounds is for the more active diastereomer. The data for the enantiopure compounds is for the more active isomer.

TABLE 1

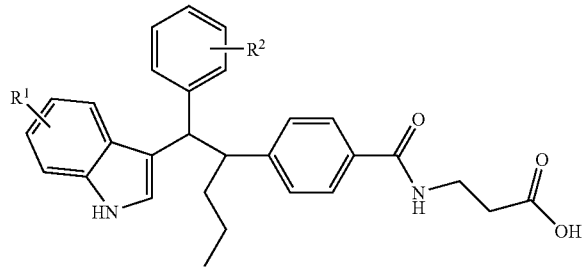

| EXAMPLE | R$^1$ | R$^2$ | enantiopurity | LC-MS data |
|---|---|---|---|---|
| 3 | H | 4-MeO | racemic | LC1 3.47 min. (M + H) 485 |
| 4 | 5-Cl | 4-MeO | racemic | LC1 3.60 min. (M + H) 519 |
| 5 | 7-Cl | 4-MeO | racemic | LC1 3.60 min. (M + H) 519 |
| 6 | 6-Cl | 4-MeO | racemic | LC1 3.62 min. (M + H) 519 |
| 7 | 5-CF$_3$O | 4-MeO | enantiopure | LC1 3.70 min. (M + H) 569 |
| 8 | 5-Bu, 7-Me | 4-MeO | racemic | LC1 4.00 min. (M + H) 555 |
| 9 | 5-Me, 7-F | 4-MeO | racemic | LC1 3.61 min. (M + H) 517 |
| 10 | 5,7-diCl | 4-MeO | racemic | LC1 3.76 min. (M + H) 553 |
| 11 | 7-Me | 4-MeO | racemic | LC1 3.57 min. (M + H) 499 |
| 12 | 5,7-diMe | 4-MeO | racemic | LC1 3.66 min. (M + H) 513 |
| 13 | 5-CF$_3$O | 4-Cl | racemic | LC1 3.93 min. (M + H) 573 |
| 14 | 5,7-diCl | 4-CF$_3$O | enantiopure | LC1 4.04 min. (M + H) 607 |
| 15 | 4,6-diCl | 4-CF$_3$O | racemic | LC1 3.99 min. (M + H) 557 |
| 16 | 5,7-diCl | 2-CF$_3$, 4-Cl | racemic | LC1 4.21 min. (M + H) 625 |
| 17 | 7-Cl | 4-Cl | enantiopure | LC1 3.81 min. (M + H) 523 |
| 18 | 6,7-diCl | 4-Cl | enantiopure | LC1 3.93 min. (M + H) 557 |
| 19 | 7-Cl | 4-CF$_3$O | enantiopure | LC1 3.92 min. (M + H) 573 |
| 20 | 6,7-diCl | 3,4-diCl | racemic | LC3 2.63 min. (M + H) 591 |
| 21 | 5,7-diF | 3,4-diCl | racemic | LC3 2.48 min. (M + H) 559 |
| 22 | 5,7-diCl | 3-CF$_3$O | enantiopure | LC2 1.31 min. (M + H) 607 |
| 23 | 6,7-diCl | 3-CF$_3$O | enantiopure | LC2 1.31 min. (M + H) 607 |
| 24 | 5,7-diF | 3-CF$_3$O | enantiopure | LC2 1.28 min. (M + H) 575 |
| 25 | 5-Me, 7-F | 3-CF$_3$ | racemic | LC2 1.28 min. (M + H) 555 |
| 26 | 6,7-diCl | 4-CF$_3$O | enantiopure | LC1 4.04 min. (M + H) 607 |
| 27 | 5-Me, 7-F | 4-CF$_3$O | enantiopure | LC1 3.89 min. (M + H) 571 |
| 28 | 5,7-diCl | 3,4-diCl | enantiopure | LC3 2.65 min. (M + H) 591 |
| 29 | 5-Me, 7-F | 3,4-diCl | enantiopure | LC3 2.54 min. (M + H) 555 |
| 30 | 7-Cl | 3,4-diCl | enantiopure | LC3 2.49 min. (M + H) 557 |
| 31 | 7-Cl | 3,4-diF | enantiopure | LC3 2.36 min. (M + H) 525 |
| 32 | 6,7-diCl | 3,4-diF | enantiopure | LC3 2.41 min. (M + H) 559 |
| 33 | 5,7-diF | 3,4-diF | enantiopure | LC3 2.30 min. (M + H) 527 |
| 34 | 7-F | 3,4-diCl | enantiopure | LC3 2.42 min. (M + H) 541 |
| 35 | 5,7-diCl | 3,4-diF | enantiopure | LC3 2.48 min. (M + H) 559 |
| 36 | 5-CN | 4-Cl | enantiopure | LC1 3.53 min. (M + H) 514 |
| 37 | 5-MeS | 4-Cl | enantiopure | LC1 3.71 min. (M + H) 535 |
| 38 | 5,7-diCl | 3-Cl | enantiopure | LC2 1.27 min. (M + H) 557 |
| 39 | 5-Me | 4-Cl | enantiopure | LC1 3.74 min. (M + H) 503 |
| 40 | 5-Cl, 7-Me | 4-Cl | enantiopure | LC1 3.84 min. (M + H) 537 |
| 41 | 6,7-diCl | 3-Cl | enantiopure | LC2 1.27 min. (M + H) 557 |
| 42 | 5,7-diMe | 4-Cl | enantiopure | LC1 3.82 min. (M + H) 517 |
| 43 | 7-F | 4-Cl | enantiopure | LC1 3.68 min. (M + H) 507 |
| 44 | 5,7-diF | 4-Cl | enantiopure | LC1 3.71 min. (M + H) 525 |

TABLE 1-continued

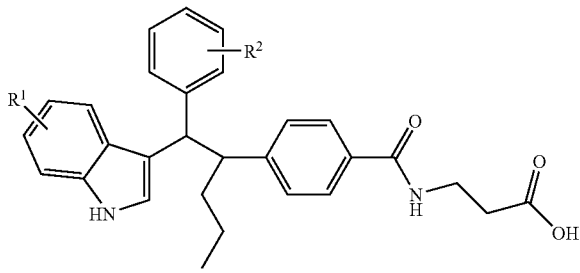

| EXAMPLE | R¹ | R² | enantiopurity | LC-MS data |
|---|---|---|---|---|
| 45 | 7-Cl | 3-Cl | enantiopure | LC2 1.25 min. (M + H) 523 |
| 46 | 5-Me, 7-F | 3-Cl | enantiopure | LC2 1.25 min. (M + H) 521 |
| 47 | 7-CF₃ | 3-Cl | enantiopure | LC2 1.26 min. (M + H) 557 |
| 48 | 5,7-diF | 3-Cl | enantiopure | LC2 1.24 min. (M + H) 525 |
| 49 | 5,7-diCl | 3-CF₃ | enantiopure | LC2 1.30 min. (M + H) 591 |
| 50 | 6,7-diCl | 3-CF₃ | enantiopure | LC2 1.30 min. (M + H) 591 |
| 51 | 5,7-diF | 3-CF₃ | enantiopure | LC2 1.27 min. (M + H) 559 |
| 52 | 5-Me, 7-F | 3,4-diF | enantiopure | LC3 2.37 min. (M + H) 523 |
| 53 | 5,7-diCl | 4-CF₃ | enantiopure | LC2 1.31 min. (M + H) 591 |
| 54 | 5,7-diF | 4-CF₃ | enantiopure | LC2 1.27 min. (M + H) 559 |
| 55 | 5-Me, 7-F | 4-CF₃ | enantiopure | LC2 1.28 min. (M + H) 555 |
| 56 | 5-Cl | 4-CF₃ | enantiopure | LC2 1.28 min. (M + H) 557 |
| 57 | 5,7-diCl | 3-F, 4-Cl | enantiopure | LC2 1.28 min. (M + H) 575 |
| 58 | 5-Me, 7-F | 3-F, 4-Cl | enantiopure | LC2 1.26 min. (M + H) 539 |
| 59 | 5-Me, 7-F | 3,5-diF | enantiopure | LC3 2.38 min. (M + H) 523 |
| 60 | 5,7-diCl | 3,5-diF | enantiopure | LC3 2.43 min. (M + H) 559 |
| 61 | 5,7-diCl | 4-Me | enantiopure | LC2 1.29 min. (M + H) 537 |
| 62 | 5-Me, 7-F | 4-Me | enantiopure | LC2 1.27 min. (M + H) 501 |
| 63 | 5-Cl, 7-Me | 4-Me | enantiopure | LC2 1.28 min. (M + H) 517 |
| 64 | 5,7-diCl | 3,4-diMe | enantiopure | LC2 1.28 min. (M + H) 551 |
| 65 | 5-Me, 7-F | 3,4-diMe | enantiopure | LC2 1.26 min. (M + H) 515 |
| 66 | 5-Cl, 7-Me | 3,4-diMe | enantiopure | LC2 1.27 min. (M + H) 531 |
| 67 | 5-Cl, 7-F | 4-Cl | enantiopure | LC1 3.86 min. (M + H) 541 |
| 68 | 5-CF₃O | 4-MeO, 3-Cl | racemic | LC1 3.76 min. (M + H) 603 |

The compounds in TABLE 2 were prepared using the chemistry described in EXAMPLES 1 and 2. The data is for the more active isomer.

TABLE 2

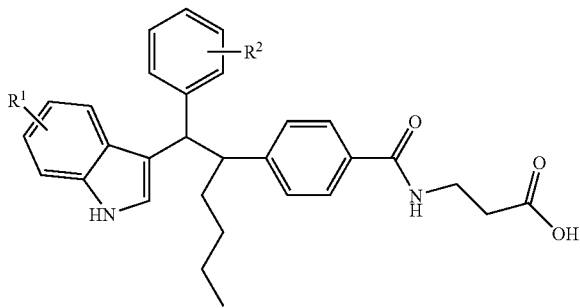

| EXAMPLE | R¹ | R² | enantiopurity | LC-MS data |
|---|---|---|---|---|
| 69 | 5-CF₃O | 4-MeO | enantiopure | LC1 3.81 min. (M + H) 583 |
| 70 | 5,7-diCl | 4-MeO | enantiopure | LC1 3.89 min. (M + H) 567 |
| 71 | 7-CF₃ | 4-MeO | enantiopure | LC1 3.78 min. (M + H) 567 |
| 72 | 4,7-diCl | 4-MeO | enantiopure | LC1 3.85 min. (M + H) 567 |
| 73 | 5,7-diF | 4-MeO | enantiopure | LC1 3.69 min. (M + H) 535 |
| 74 | 7-Et | 4-MeO | enantiopure | LC1 3.77 min. (M + H) 527 |

TABLE 2-continued

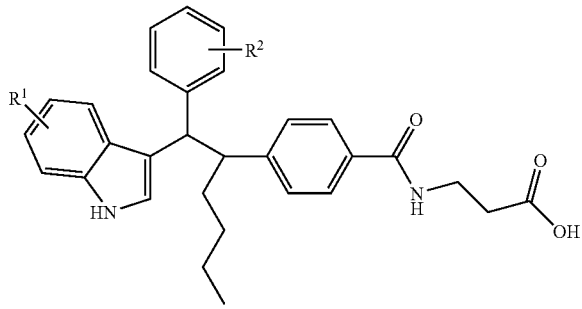

| EXAMPLE | R¹ | R² | enantiopurity | LC-MS data |
|---|---|---|---|---|
| 75 | 5-Cl, 7-Me | 4-MeO | enantiopure | LC1 3.80 min. (M + H) 547 |
| 76 | 5-Bu, 7-Me | 4-MeO | enantiopure | LC1 4.15 min. (M + H) 569 |
| 77 | 5-Me, 7-F | 4-MeO | enantiopure | LC1 3.74 min. (M + H) 531 |
| 78 | 6,7-diCl | 4-MeO | enantiopure | LC1 3.82 min. (M + H) 567 |
| 79 | 5,7-diCl | 4-Cl | enantiopure | LC1 4.07 min. (M + H) 571 |
| 80 | 5-Me, 7-F | 4-Cl | enantiopure | LC1 3.93 min. (M + H) 535 |
| 81 | 5-Me, 7-F | H | enantiopure | LC1 3.79 min. (M + H) 501 |
| 82 | 5,7-diCl | 3,4-diF | enantiopure | LC1 2.54 min. (M + H) 573 |

The compounds in TABLE 3 were prepared using the chemistry described in EXAMPLES 1 and 2. All compounds, except EXAMPLE 88, are enantiopure. Data is for the more active isomer.

TABLE 3

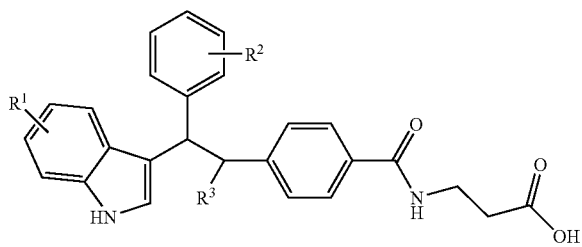

| EXAMPLE | R¹ | R² | R³ | LC-MS data |
|---|---|---|---|---|
| 83 | 5-CF₃O | 4-Cl | Me | LC1 3.71 min. (M + H) 545 |
| 84 | 5-CF₃O | 4-MeO | Me | LC1 3.47 min. (M + H) 541 |
| 85 | 7-CF₃O | 4-Cl | Me | LC1 3.72 min. (M + H) 545 |
| 86 | 6-CF₃O | 4-Cl | Me | LC1 3.72 min. (M + H) 545 |
| 87 | 5-CF₃O | 4-MeO | Et | LC1 3.62 min. (M + H) 555 |
| 88 | 5,7-diCl | 4-MeO | CF₃(CH₂)₃— (racemic) | LC1 3.78 min. (M + H) 621 |
| 89 | 5,7-diCl | 4-Cl | Et | LC1 2.46 min. (M + H) 543 |
| 90 | 5-Me, 7-F | 4-Cl | Et | LC3 2.36 min. (M + H) 507 |

EXAMPLE 91

4-{1-[(3-chloro-4-methoxyphenyl)(5,7-dichloro-1H-indol-3-yl)methyl]pentyl}benzoyl)-β-alanine

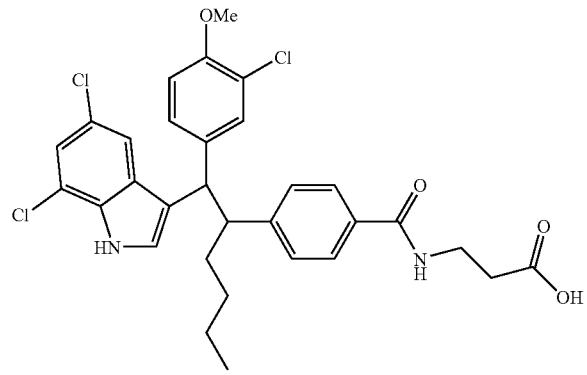

Step A. tert-Butyl N-(4-{1-[1-(3-chloro-4-methoxyphenyl)-3-oxopropyl]pentyl}benzoyl)-β-alaninate N-Chlorosuccinamide (40 mg, mmol) was added to an acetonitrile solution (2 ml) containing enantiopure tert-butyl N-(4-{1-[1-(4-methoxyphenyl)-3-oxopropyl]pentyl}benzoyl)-β-alaninate (20 mg, 0.42 mol), which was prepared following the procedure described in EXAMPLE 1. The solution was then heated in a screw cap tube for 35 minutes at 85° C. The solution was concentrated and the residue purified by PTLC using an EtOAC/hexanes eluent to give a mixture of compounds containing the title compound and the corresponding 3,5-diCl analog (~30% by NMR). LC1 4.00 min. (M+H) 460, di Cl LC1 4.15 min. (M+H) 494 selected data $^1$H NMR (400 MHz, CDCl$_3$): δ 9.35 (s, 1H); 7.72 (d, J=8.2 Hz, 2H); 7.23-7.15 (m, 3H); 6.86 (d, J=8.4 Hz, 2H); 3.88 (S, 3H); 3.68 (q, J=5.9 Hz, 2H); 3.29-3.23 (m, 1H); 2.75-2.65 (m, 1H); 2.56-2.50 (m, 2H); 2.39-2.31 (m, 1H); 1.46 (s, 9H); 0.66 (t, 3H).

Step B. N-(4-{1-[(3-Chloro-4-methoxyphenyl)(5,7-dichloro-1H-indol-3-yl)methyl]pentyl}benzoyl)-β-alanine The title compound was prepared from the intermediate from Step A following the procedure described in EXAMPLE 1, Step C. The crude material was purified by HPLC to give the title compound (along with the corresponding 3,5-diCl analog). $^1$H NMR (400 MHz, CD$_3$CN): δ 9.35 (s, 1H); 7.56 (d, J=8.2 Hz, 2H); 7.49 (d, J=2.4 Hz, 2H); 7.41 (dd, J=2.2, 8.5 Hz, 1H); 7.37 (d, J=8.3 Hz, 2H); 7.29 (d, J=2.5 Hz, 1H); 7.08 (d, J=1.7 Hz, 1H); 7.04 (broad s, 1H); 7.00 (d, J=8.5 Hz, 1H); 4.44 (d, J=11.7 Hz, 1H); 3.83 (s, 3H); 3.53-3.47 (m, 3H); 2.53 (t, J=6.7 Hz, 3H); 1.51-1.43 (m, 2H); 1.22-0.84 (m, 5H); 0.69 (t, J=7.3 Hz, 3H). LC1 3.99 min. (M+H) 601

EXAMPLE 92

N-(4-{1-[(5,7-dichloro-1H-indol-3-yl)(3,5-dichloro-4-methoxyphenyl)methyl]pentyl}benzoyl)-β-alanine

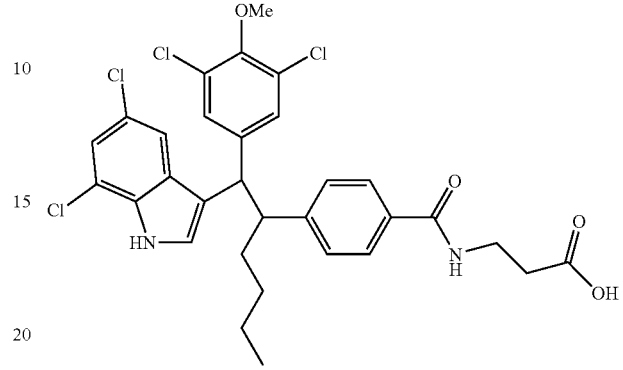

The title compound was isolated in the preparation described in EXAMPLE 91. $^1$H NMR (400 MHz, CD$_3$CN): δ 9.41 (s, 1H); 7.56-7.52 (m, 5H); 7.38-7.32 (m, 3H); 7.10 (d, J=1.7 Hz, 1H); 7.03 (broad s, 1H); 4.46 (d, J=11.7 Hz, 1H); 3.81 (s, 3H); 3.54-3.48 (m, 4H); 2.53 (t, J=6.7 Hz, 3H); 1.52-1.46 (m, 3H); 1.26-0.86 (m, 6H); 0.71 (t, J=7.3 Hz, 3H). LC1 4.17 min. (M+H) 635

INTERMEDIATE 3

Methyl 4-[(3E,Z)-2-(3-bromophenyl)-4-methoxy-1-methylbut-3-en-1-yl]benzoate

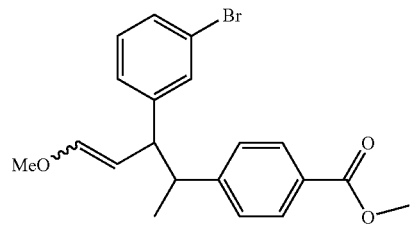

Step A. 4-Methoxybenzyl (3-bromophenyl)acetate

A DMF (30 mL) solution of (3-bromophenyl)acetic acid (2.5 g, 11.6 mmol), cesium carbonate (3.78 g, 11.6 mmol) and 4-methoxybenzyl chloride (1.82 g, 11.6 mmol) was stirred overnight at room temperature. The solution was then partitioned between ethyl acetate and water. The organic phase was washed with water (3×), brine and dried over magnesium sulfate. The solution was filtered, concentrated and the residue purified by silica gel chromatography using a hexanes/ethyl acetate gradient to give the title compound. $^1$H NMR (400 MHz, CDCl$_3$): δ 7.43-7.39 (m, 2H); 7.29-7.24 (m, 2H); 7.20-7.16 (m, 2H); 6.90-6.86 (m, 2H); 5.07 (s, 2H); 3.81 (s, 3H); 3.60 (s, 2H). LC1 3.70 min.

Step B. Methyl 4-{2-(3-bromophenyl)-3-[(4-methoxybenzyl)oxy]-1-methyl-3-oxopropyl}benzoate LHMDS (1.0M THF, 2.6 mL) was added dropwise to a −78° C. THF (4 mL) solution containing the intermediate from Step A (0.827 g, 2.47 mmol). After stirring 10 minutes a THF (4 mL) solution containing methyl 4-(1-bromoethyl) benzoate (0.6 g, 2.47 mmol) was added dropwise. The solution was allowed to warm to room temperature. After 1.5 hours the solution was partitioned between ethyl acetate and aqueous 1N HCl. The organic phase was washed with water, brine and dried over magnesium sulfate. The solution was filtered and the residue purified by silica gel chromatography using a hexanes/ethyl acetate gradient to give the title compounds as a 1.67/1 mixture of diastereomers. $^1$H NMR (400 MHz, CDCl$_3$): selected data δ 5.16 (d, J=12.0 Hz); 5.01 (d, J=12.0 Hz); 4.82 (d, J=12.0 Hz); 4.64 (d, J=11.9 Hz); 1.34 (d, J=6.8 Hz); 1.02 (d, J=7.0 Hz). Minor diastereomer: LCMS1 4.08 min (M+Na)=519. Major diastereomer: LC1 4.19 min (M+Na)=519.

Step C. 2-(3-Bromophenyl)-3-[4-(methoxycarbonyl) phenyl]butanoic acid

The intermediate from Step B (0.8 g, 1.6 mmol) was treated with 4-methoxy benzene (2 mL) and trifluoroacetic acid (15 mL). After stirring for 1.5 hours the solution was concentrated and the residue purified by silica gel chromatography using a hexanes/ethyl acetate gradient (containing 0.05% acetic acid) to give the title compounds as mixture of diastereomers. $^1$H NMR (400 MHz, CDCl$_3$): selected data δ 3.90 (s); 3.85 (s); 3.72-3.64 (m); 3.52-3.42 (m); 1.39 (d, J=6.8 Hz); 1.03 (d, J=7.0 Hz). LCMS1 3.34 min. (M+H)=377. LC1 3.57 min. (M+H)=377.

Step D. Methyl 4-[2-(3-bromophenyl)-3-hydroxy-1-methylpropyl]benzoate

BOP (152 mg, 0.345 mmol) was added to a THF (2 mL) solution containing the intermediate from Step C (100 mg, 0.265 mmol) and DIEA (0.06 ml, 0.344 mmol). After stirring for 5 minutes sodium borohydride (20 mg, 0.53 mmol) was added to the solution. The solution was stirred for 15 minutes and then partitioned between aqueous 1N HCl and ethyl acetate. The organic phase was washed with brine and dried over magnesium sulfate. The solution was filtered and the residue purified by silica gel chromatography using a hexanes/ethyl acetate gradient to give the title compounds as a mixture of diastereomers. A portion of the isolated material also contained single diastereomeric products. Diastereomer A, faster eluting on silica gel: $^1$H NMR (400 MHz, CDCl$_3$): δ 8.01 (d, J=8.3 Hz, 2H); 7.48-7.40 (m, 2H); 7.33 (d, J=8.3 Hz, 2H); 7.26-7.19 (m, 2H); 3.92 (s, 3H); 3.59-3.47 (m, 2H); 3.10-3.04 (m, 1H); 2.92-2.88 (m, 1H); 1.05 (d, J=6.9 Hz, 3H). LC1 3.60 min. (M−H2O)=345. Diastereomer B, slower eluting on silica gel: $^1$H NMR (400 MHz, CDCl$_3$): δ 7.82 (d, J=8.3 Hz, 2H); 7.17-7.13 (m, 1H); 7.04-6.96 (m, 4H); 6.85 (d, J=7.7 Hz, 1H); 4.00-3.88 (m, 2H); 3.87 (s, 3H); 3.26-3.18 (m, 1H); 3.02-2.96 (m, 1H); 1.37 (d, J=6.9 Hz, 3H). LC1 3.40 min. (M−H$_2$O)=345.

Step E. Methyl 4-[2-(3-bromophenyl)-1-methyl-3-oxopropyl]benzoate

Dess-Martin periodinane (0.72 g, 1.7 mmol) was added to a dichloromethane solution (5 ml) of diastereomer A from Step D (0.476 g, 1.31 mmol). After 1 hour the solution was concentrated and the residue purified by silica gel chromatography using a hexanes/ethyl acetate gradient to give the title compound. $^1$H NMR (400 MHz, CDCl$_3$): δ 9.56 (d, J=2.4 Hz, 1H); 8.00 (d, J=8.2 Hz, 2H); 7.50-7.46 (m, 1H); 7.40-7.37 (m, 1H); 7.31 (d, J=8.2 Hz, 2H); 7.30-7.28 (m, 1H); 7.07 (d, J=8.2 Hz); 3.91 (s, 3H); 3.81-3.76 (m, 1H); 3.64-3.53 (m, 1H); 1.11 (d, J=7.0 Hz, 3H). LC1 3.58 min. (M+1)=358.

Step F. Methyl 4-[(3-E,Z)-2-(3-bromophenyl)-4-methoxy-1-methylbut-3-en-1-yl]benzoate Potassium bis(trimethylsilyl)amide (0.5M in toluene, 8.6 ml, 4.3 mmol) was added dropwise to a THF solution (18 ml) of (methoxymethyl)triphenylphosphonium chloride (1.5 g, 4.38 mmol) at −78° C. The solution was then stirred at 0° C. for 45 minutes. A THF solution (4 ml) of the intermediate from Step E (0.626 g, 1.73 mmol) was added dropwise. The solution was then stirred overnight at room temperature. The reaction was partitioned between EtOAc and water. The organic phase was washed with brine, dried over MgSO$_4$, filtered and concentrated. The residue was purified by silica gel chromatography using a hexanes/ethyl acetate gradient to give the title compound as a mixture of E,Z isomers. A portion of the isolated material was a single isomer (major): $^1$H NMR (500 MHz, CDCl$_3$): δ 7.96 (d, J=8.7 Hz, 2H); 7.34 (m, 2H); 7.16 (m, 3H); 7.06 (m, 1H); 5.99 (d, J=12.5 Hz, 1H); 4.66 (dd, J=9.1, 12.5 Hz, 1H); 3.91 (s, 3H); 3.33 (s, 3H); 3.24 (t, J=9.1 Hz, 1H); 3.05 (m, 1H); 1.12 (d, J=6.9 Hz, 3H). LC1 3.87 min. (M+1)=389

INTERMEDIATE 4

Methyl N-{4-[2-(3-bromophenyl)-2-(1H-indol-3-yl)-1-methylethyl]benzoyl}-β-alaninate

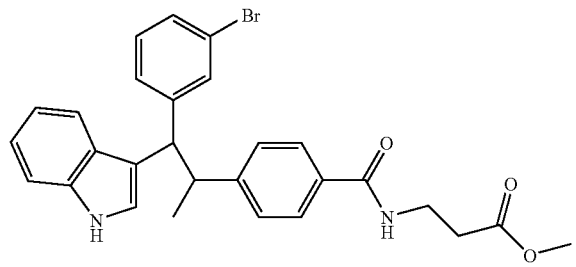

The title compound was prepared from INTERMEDIATE 3 using the Fischer indole chemistry described in EXAMPLE 1 Step C followed by the hydrolysis condition in INTERMEDIATE 2 Step G and the beta alanine coupling described in EXAMPLE 1 Step A. $^1$H NMR (500 MHz, CD$_3$CN): δ 9.00 (s, 1H); 7.66 (t, J=1.8 Hz, 1H); 7.55 (d, J=8.4 Hz, 2H); 7.50 (t, J=6.8 Hz, 2H); 7.41 (d, J=8.5 Hz, 2H); 7.32 (m, 1H); 7.23-7.18 (m, 1H); 7.15 (d, J=2.5 Hz, 1H); 7.02-6.98 (m, 2H); 6.94-6.92 (m, 1H); 4.52 (d, J=11.6 Hz, 1H); 3.78-3.69 (m, 1H); 3.60 (s, 3H); 3.51 (q, J=6.5 Hz, 2H); 2.53 (t, J=6.7 Hz, 2H); 1.09 (d, J=6.8 Hz, 3H). LC1 3.32 min. (M+1)=519.

EXAMPLE 93

N-{4-[2-{3-[(1E)-hex-1-en-1-yl]phenyl}-2-(1H-indol-3-yl)-1-methylethyl]benzoyl}-β-alanine

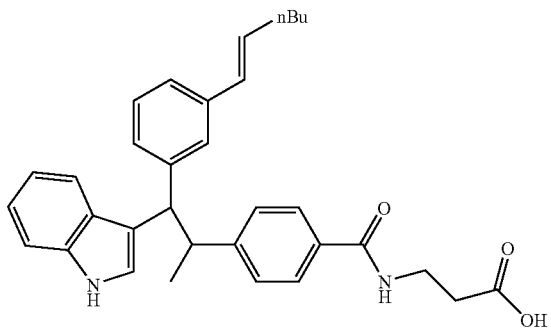

Step A. Methyl N-{4-[2-{3-[(1E)-hex-1-en-1-yl]phenyl}-2-(1H-indol-3-yl)-1-methylethyl]benzoyl}-β-alaninate A solution of 1,2-dimethoxyethane (2 ml) and water (0.5 ml) containing the INTERMEDIATE 4 (50 mg, 0.1 mmol), (1E)-hex-1-en-1-ylboronic acid (51 mg, 0.4 mmol), potassium carbonate (62 mg, 0.45 mmol) and Pd(PPh$_3$)$_4$ (10 mg, 0.009 mmol) was heated at reflux for 1 hour. The solution was concentrated and partitioned between EtOAc and aqueous 1N HCl. The organic phase was washed with brine, dried over Na$_2$SO$_4$, filtered and concentrated. The residue was purified by reverse phase HPLC to give the title compound. LC2 1.30 min. (M+1)=523

Step B. N-{4-[2-{3-[(1E)-Hex-1-en-1-yl]phenyl}-2-(1H-indol-3-yl)-1-methylethyl]benzoyl}-β-alanine The title compound was prepared from the intermediate from Step A using the hydrolysis conditions described in INTERMEDIATE 2, Step G. The crude material was purified by HPLC. $^1$H NMR (500 MHz, CD$_3$CN): δ 8.97 (s, 1H); 7.55 (d, J=8.3 Hz, 2H); 7.52 (d, J=7.9 Hz, 1H); 7.49 (s, 1H); 7.43 (d, J=8.3 Hz, 2H); 7.33 (d, J=7.5 Hz, 1H); 7.20 (t, J=7.6 Hz, 2H); 7.14 (m, 2H); 7.07 (broad s, 1H); 6.99-6.96 (m, 1H); 6.92-6.89 (m, 1H); 6.40-6.25 (m, 2H); 4.50 (d, J=11.5 Hz, 1H); 3.77-3.69 (m, 1H); 3.49 (q, J=6.4 Hz, 2H); 2.53 (dd, J=14.4, 21.1 Hz, 26H); 1.47-1.33 (m, 4H); 1.08 (d, J=6.8 Hz, 3H); 0.92 (t, J=7.2 Hz, 3H). LC1 3.72 min. (M+1)=509.

EXAMPLE 94

N-{4-[2-(3-hexylphenyl)-2-(1H-indol-3-yl)-1-methylethyl]benzoyl}-β-alanine

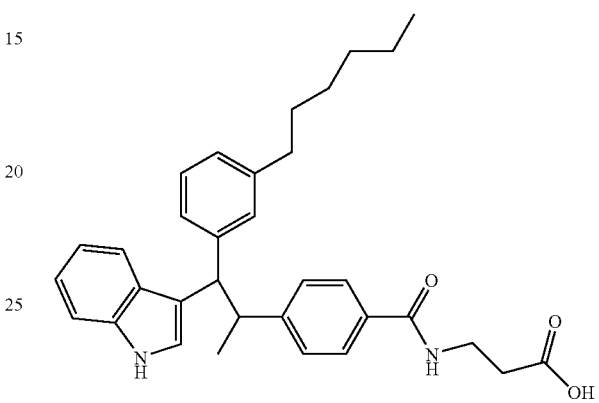

A methanol solution (2 ml) containing EXAMPLE 93 (5 mg) and 10% palladium/C (spatula tip) was stirred under a hydrogen atmosphere (balloon) until no starting material remained by HPLC analysis. The solution was filtered, concentrated and the residue purified by HPLC to give the title compound. $^1$H NMR (500 MHz, CD$_3$CN): δ 8.98 (s, 1H); 7.53 (t, J=8.8 Hz, 3H); 7.41 (d, J=8.3 Hz, 2H); 7.35 (s, 1H); 7.27 (d, J=7.7 Hz, 1H); 7.21-7.15 (m, 2H); 7.11 (m, 2H); 6.99-6.95 (m, 2H); 6.92-6.88 (m, 1H); 4.47 (d, J=11.5 Hz, 1H); 3.76-3.68 (m, 1H); 3.50 (q, J=6.4 Hz, 2H); 2.59-2.51 (m, 4H); 1.57 (t, J=6.9 Hz, 2H); 1.27 (m, 4H); 1.07 (d, J=6.8 Hz, 3H); 0.86 (t, J=6.9 Hz, 3H). LC1 3.76 min. (M+H) 511.

The compounds in TABLE 4 were prepared as described for EXAMPLES 93 and 94. Data is for the more active isomer.

TABLE 4

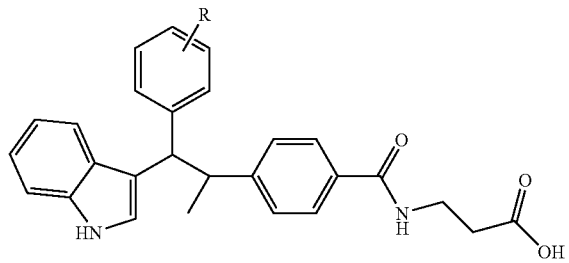

| EXAMPLE | R | enantiopurity | LC-MS data |
|---|---|---|---|
| 95 | 3-cyclohex-1-enyl | racemic | LC1 3.58 min. (M + H) 507 |
| 96 | 3-cyclohexyl | racemic | LC1 3.62 min. (M + H) 509 |
| 97 | 4-(4'-$^t$Bu-cyclohex-1'-enyl) | enantiopure | LC1 4.45 min. (M + H) 563 |
| 98 | 4-(4'-$^t$Bu-cyclohexl) | enantiopure (mix of cis and trans) | LC1 4.47 min. (M + H) 565 |
| 99 | 4-hex-1-enyl | enantiopure | LC1 4.04 min. (M + H) 509 |
| 100 | 4-hexyl | enantiopure | LC1 4.14 min. (M + H) 511 |

EXAMPLES 101/102

N-(4-{1-[(4-chlorophenyl)(5,7-dichloro-1-methyl-1H-indol-3-yl)methyl]butyl}benzoyl)-β-alanine

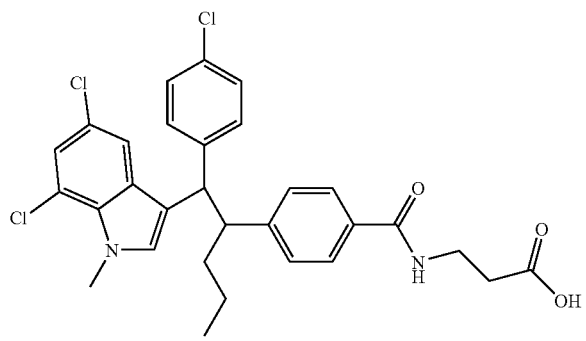

Step A. Methyl N-(4-{1-[(4-chlorophenyl)(5,7-dichloro-1-methyl-1H-indol-3-yl)methyl]butyl}benzoyl)-β-alaninate A solution of KOtBu (1.0M THF, ca. 3 drops, 0.045 ml) was added to a dimethylacetamide solution (2 ml) of the intermediate from EXAMPLE 1, Step C (faster eluting enantiomer on ChiralPak AD 10% EtOH/Heptane, 4 mg, 0.007 mmol). Methyl iodide (three drops, excess) was then added dropwise. The progress of the reaction during the addition was monitored by MS-HPLC in order to minimize over alkylation. The reaction was quenched with aqueous 1N HCl. The mixture was extracted with EtOAc and the combined organics washed with water and brine. The solution was then dried over $Na_2SO_4$, filtered and concentrated to give the title compound which was used without further purification. LCMS1 4.40 min. (M+H)=585. The procedure was also carried out as described on the intermediate from Example 1, Step C (slower eluting enantiomer). LCMS1 4.39 min. (M+H)=585

Step B. N-(4-{1-[(4-Chlorophenyl)(5,7-dichloro-1-methyl-1H-indol-3-yl)methyl]butyl}benzoyl)-β-alanine Using the hydrolysis conditions described in INTERMEDIATE 2, Step G the title compounds were prepared. Data for the faster eluting enantiomer: $^1$H NMR (500 MHz, $CD_3CN$): δ 7.56 (d, J=8.3 Hz, 2H); 7.46 (d, J=8.4 Hz, 2H); 7.42 (d, J=1.9 Hz, 1H); 7.37 (d, J=8.3 Hz, 2H); 7.31 (d, J=8.4 Hz, 2H); 7.16 (s, 1H); 7.06 (broad s, 1H); 7.00 (d, J=1.8 Hz, 1H); 4.46 (d, J=11.6 Hz, 1H); 3.92 (s, 3H); 3.52-3.45 (m, 3H); 2.54 (t, J=6.7 Hz, 2H); 1.50-1.36 (m, 2H); 1.00-0.90 (m, 2H); 0.69 (t, J=7.3 Hz, 3H). LCMS1 4.17 min. (M+H)=571

Data for the slower eluting enantiomer: $^1$H NMR (500 MHz, $CD_3CN$): δ 7.56 (d, J=8.3 Hz, 2H); 7.46 (d, J=7.8 Hz, 2H); 7.42 (d, J=1.8 Hz, 1H); 7.37 (d, J=8.3 Hz, 2H); 7.31 (d, J=8.4 Hz, 2H); 7.15 (s, 1H); 7.07 (broad s, 1H); 7.00 (d, J=1.8 Hz, 1H); 4.45 (d, J=11.6 Hz, 1H); 3.91 (s, 3H); 3.51-3.44 (m, 3H); 2.53 (t, J=6.6 Hz, 2H); 1.49-1.35 (m, 2H); 0.98-0.88 (m, 2H); 0.68 (t, J=7.3 Hz, 3H). LCMS1 4.16 min. (M+H)=571

The compounds in TABLE 5 were prepared as described in EXAMPLES 101 and 102.

TABLE 5

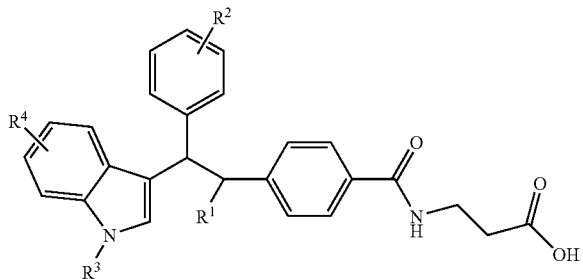

| EXAMPLE | $R^1$ | $R^2$ | $R^3$ | $R^5$ | LC-MS data |
|---|---|---|---|---|---|
| 103 (racemic) | Me | 4-Cl | Bn | H | LC1 3.90 min. M + H = 511 |
| 104 (racemic) | n-Pr | 4-Cl | n-Pr | 5,7-diCl | LC1 4.38 min. (M + H) 599 |
| 105 (enantiomer 1) | n-Pr | 4-$CF_3O$ | Me | 5,7-diCl | LC1 4.20 min. (M + H) 621 |
| 106 (enantiomer 2) | n-Pr | 4-$CF_3O$ | Me | 5,7-diCl | LC1 4.20 min. (M + H) 621 |
| 107 (enantiomer 1) | n-Bu | 4-MeO | Me | 5,7-diCl | LC1 4.02 min. (M + H) 581 |
| 108 (enantiomer 2) | n-Bu | 4-MeO | Me | 5,7-diCl | LC1 4.05 min. (M + H) 581 |

The compounds shown in TABLE 6 were prepared from 2-acetyl-6-methoxynaphthalene using the chemistry described in EXAMPLE 1. Data is for the more active isomer.

TABLE 6

| EXAMPLE | R¹ | enantiopurity | LC-MS data |
|---|---|---|---|
| 109 | 7-Cl | racemic | LC2 1.26 min. (M + H) 569 |
| 110 | 5-Cl | racemic | LC2 1.26 min. (M + H) 569 |
| 111 | 5-CF₃O | racemic | LC2 1.27 min. (M + H) 619 |
| 112 | 5,7-diCl | enantiopure | LC2 1.28 min. (M + H) 603 |
| 113 | 6,7-diCl | enantiopure | LC2 1.27 min. (M + H) 603 |
| 114 | 5-Me, 7-F | enantiopure | LC2 1.26 min. (M + H) 567 |
| 115 | 7-CF₃ | enantiopure | LC2 1.27 min. (M + H) 603 |

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/−compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prism® from GraphPad. The IC$_{50}$ values were calculated using non-linear regression analysis assuming single site competition. IC$_{50}$ values for the compounds of the invention are generally in the range of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

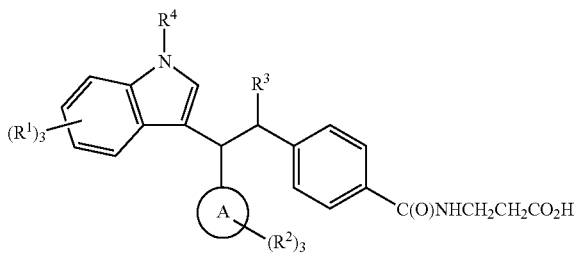

or a pharmaceutically acceptable salt thereof wherein:
ring A represents a phenyl or naphthyl group;
each R¹ and R² represents H or is selected from the group consisting of halo, CN, OH, NO₂, CO₂R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of, C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo and C$_{1-6}$alkoxy;
p represents 0, 1 or 2;
each R$^a$ and R$^b$ independently represents H or C$_{1-4}$alkyl optionally substituted with 1-5 halo atoms up to perhalo; and further optionally substituted with 1 group selected from OH, oxo and C$_{1-6}$alkoxy;
R³ represents C$_{1-6}$alkyl or C$_{2-6}$alkenyl, each optionally substituted with 1-5 halo atoms up to perhalo, and further optionally substituted with 1 group selected from OH, oxo and C$_{1-6}$alkoxy, and
R⁴ represents H or C$_{1-4}$alkyl optionally substituted with 1-3 halo atoms up to perhalo and 1 phenyl ring.

2. A compound in accordance with claim 1, or a pharmaceutically acceptable salt thereof, wherein ring A represents phenyl.

3. A compound in accordance with claim 1, or a pharmaceutically acceptable salt thereof, wherein ring A represents naphthyl.

4. A compound in accordance with claim 1, or a pharmaceutically acceptable salt thereof, wherein each R¹ represents H or is selected from the group consisting of fluoro; chloro; SCH₃; CN, C$_{1-6}$alkyl, C$_{2-4}$alkenyl and C$_{1-6}$alkoxy,
wherein the alkyl and alkenyl portions of SCH₃, C$_{1-6}$alkyl, C$_{2-4}$alkenyl and C$_{1-6}$alkoxy are optionally substituted with 1-3 fluoro atoms.

5. A compound in accordance with claim 4 wherein each $R^1$ represents H or is selected from the group consisting of fluoro, chloro; $SCH_3$; CN, $C_{1-4}$alkyl and $OCH_3$,
   wherein the alkyl portions of $SCH_3$, $C_{1-4}$alkyl and $OCH_3$ are optionally substituted with 1-3 fluoro atoms.

6. A compound in accordance with claim 1, or a pharmaceutically acceptable salt thereof, wherein each $R^2$ represents H or is selected from the group consisting of: fluoro; chloro; $SCH_3$; CN, $C_{1-6}$alkyl, $C_{2-4}$alkenyl and $C_{1-6}$alkoxy,
   wherein the alkyl and alkenyl portions of $SCH_3$, $C_{1-6}$alkyl, $C_{2-4}$alkenyl and $C_{1-6}$alkoxy are optionally substituted with 1-3 fluoro atoms.

7. A compound in accordance with claim 6, or a pharmaceutically acceptable salt thereof, wherein each $R^2$ represents H or is selected from the group consisting of fluoro, chloro; $SCH_3$; CN, $C_{1-6}$alkyl, $C_{2-4}$alkenyl and $C_{1-6}$alkoxy,
   wherein the alkyl and alkenyl portions of $SCH_3$, $C_{1-6}$alkyl, $C_{2-4}$alkenyl and $C_{1-6}$alkoxy are optionally substituted with 1-3 fluoro atoms.

8. A compound in accordance with claim 7, or a pharmaceutically acceptable salt thereof, wherein each $R^2$ represents H or is selected from the group consisting of fluoro, chloro; $SCH_3$; CN, $C_{1-4}$alkyl and $OCH_3$,
   wherein the alkyl portions of $SCH_3$, $C_{1-4}$alkyl and $OCH_3$ are optionally substituted with 1-3 fluoro atoms.

9. A compound in accordance with claim 1, or a pharmaceutically acceptable salt thereof, wherein $R^3$ represents a member selected from the group consisting of: $CH_3$, ethyl, n-propyl, n-, s- and t-butyl, and allyl.

10. A compound in accordance with claim 1, or a pharmaceutically acceptable salt thereof, wherein $R^4$ is selected from the group consisting of: H, methyl, ethyl, n-propyl, n-butyl and benzyl.

11. A compound in accordance with claim 1, or a pharmaceutically acceptable salt thereof, wherein:
   ring A represents a phenyl or naphthyl group;
   each $R^1$ and $R^2$ represents H or is selected from the group consisting of halo selected from fluoro and chloro; $SCH_3$; CN, $C_{1-6}$alkyl, $C_{2-4}$alkenyl and $C_{1-6}$alkoxy,
   wherein the alkyl and alkenyl portions of $SCH_3$, $C_{1-6}$alkyl, $C_{2-4}$alkenyl and $C_{1-6}$alkoxy are optionally substituted with 1-3 fluoro atoms;
   $R^3$ represents a member selected from the group consisting of: methyl, ethyl, n-propyl, n-, s- and t-butyl, and allyl, and
   $R^4$ is selected from the group consisting of: H, methyl, ethyl, n-propyl, n-butyl and benzyl.

12. A compound in accordance with claim 1, or a pharmaceutically acceptable salt thereof, selected from the group consisting of:

TABLE A

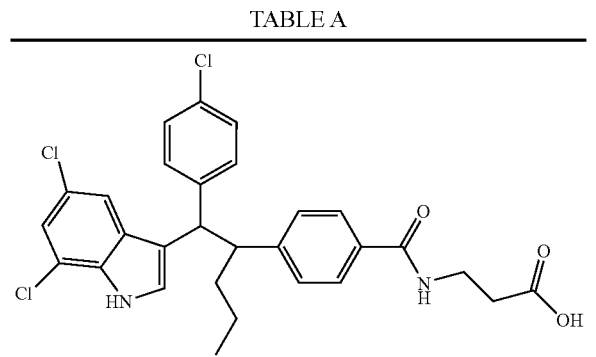

TABLE A-continued

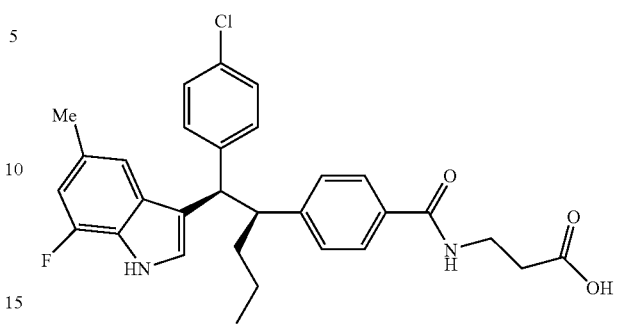

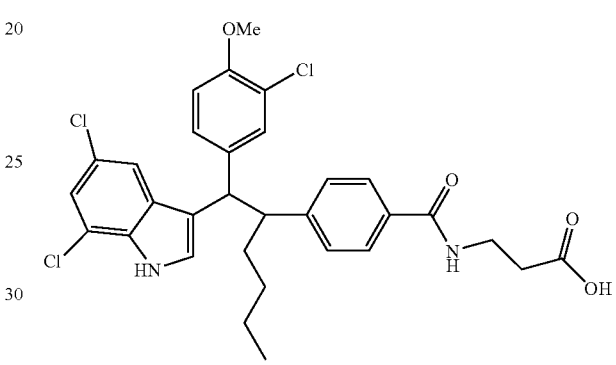

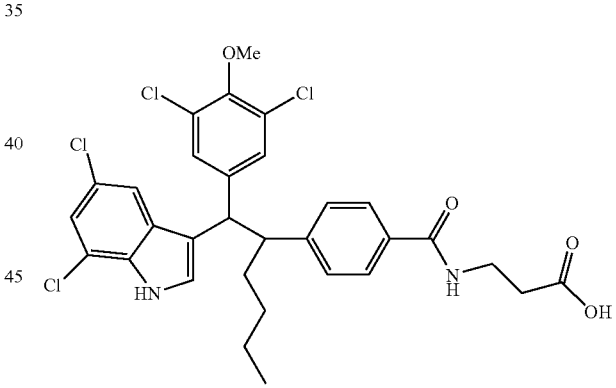

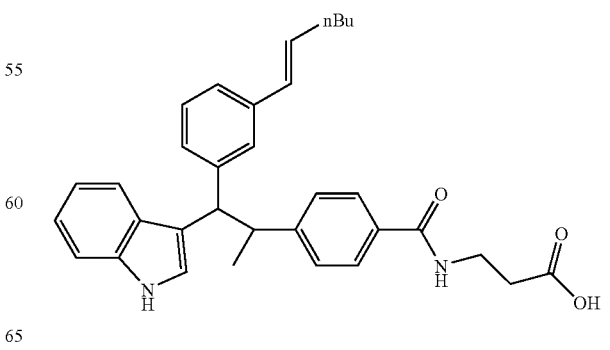

TABLE A-continued

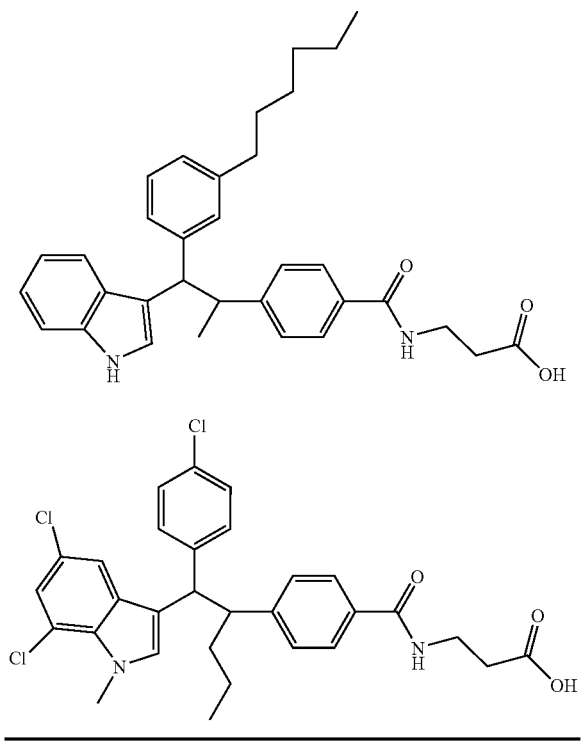

TABLE 1

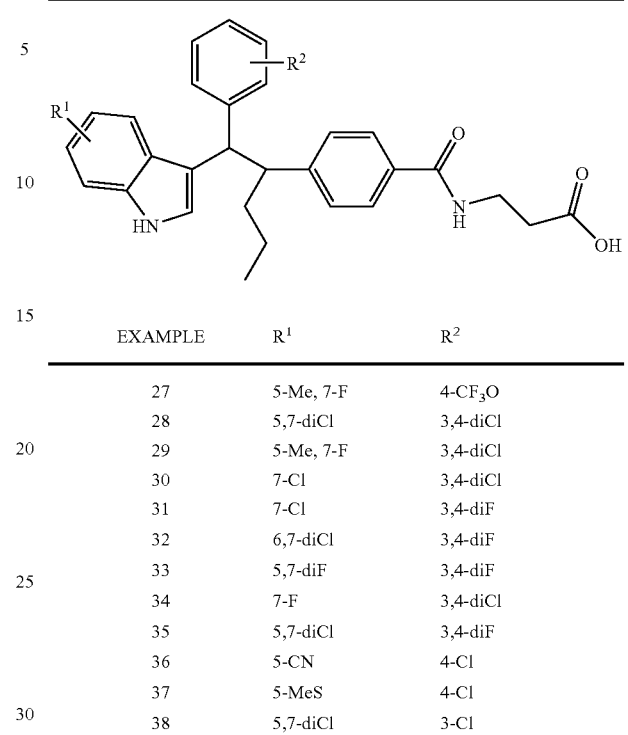

| EXAMPLE | R¹ | R² |
|---|---|---|
| 3 | H | 4-MeO |
| 4 | 5-Cl | 4-MeO |
| 5 | 7-Cl | 4-MeO |
| 6 | 6-Cl | 4-MeO |
| 7 | 5-CF₃O | 4-MeO |
| 8 | 5-Bu, 7-Me | 4-MeO |
| 9 | 5-Me, 7-F | 4-MeO |
| 10 | 5,7-diCl | 4-MeO |
| 11 | 7-Me | 4-MeO |
| 12 | 5,7-diMe | 4-MeO |
| 13 | 5-CF₃O | 4-Cl |
| 14 | 5,7-diCl | 4-CF₃O |
| 15 | 4,6-diCl | 4-CF₃O |
| 16 | 5,7-diCl | 2-CF₃, 4-Cl |
| 17 | 7-Cl | 4-Cl |
| 18 | 6,7-diCl | 4-Cl |
| 19 | 7-Cl | 4-CF₃O |
| 20 | 6,7-diCl | 3,4-diCl |
| 21 | 5,7-diF | 3,4-diCl |
| 22 | 5,7-diCl | 3-CF₃O |
| 23 | 6,7-diCl | 3-CF₃O |
| 24 | 5,7-diF | 3-CF₃O |
| 25 | 5-Me, 7-F | 3-CF₃ |
| 26 | 6,7-diCl | 4-CF₃O |

TABLE 1-continued

| EXAMPLE | R¹ | R² |
|---|---|---|
| 27 | 5-Me, 7-F | 4-CF₃O |
| 28 | 5,7-diCl | 3,4-diCl |
| 29 | 5-Me, 7-F | 3,4-diCl |
| 30 | 7-Cl | 3,4-diCl |
| 31 | 7-Cl | 3,4-diF |
| 32 | 6,7-diCl | 3,4-diF |
| 33 | 5,7-diF | 3,4-diF |
| 34 | 7-F | 3,4-diCl |
| 35 | 5,7-diCl | 3,4-diF |
| 36 | 5-CN | 4-Cl |
| 37 | 5-MeS | 4-Cl |
| 38 | 5,7-diCl | 3-Cl |
| 39 | 5-Me | 4-Cl |
| 40 | 5-Cl, 7-Me | 4-Cl |
| 41 | 6,7-diCl | 3-Cl |
| 42 | 5,7-diMe | 4-Cl |
| 43 | 7-F | 4-Cl |
| 44 | 5,7-diF | 4-Cl |
| 45 | 7-Cl | 3-Cl |
| 46 | 5-Me, 7-F | 3-Cl |
| 47 | 7-CF₃ | 3-Cl |
| 48 | 5,7-diF | 3-Cl |
| 49 | 5,7-diCl | 3-CF₃ |
| 50 | 6,7-diCl | 3-CF₃ |
| 51 | 5,7-diF | 3-CF₃ |
| 52 | 5-Me, 7-F | 3,4-diF |
| 53 | 5,7-diCl | 4-CF₃ |
| 54 | 5,7-diF | 4-CF₃ |
| 55 | 5-Me, 7-F | 4-CF₃ |
| 56 | 5-Cl | 4-CF₃ |
| 57 | 5,7-diCl | 3-F, 4-Cl |
| 58 | 5-Me, 7-F | 3-F, 4-Cl |
| 59 | 5-Me, 7-F | 3,5-diF |
| 60 | 5,7-diCl | 3,5-diF |
| 61 | 5,7-diCl | 4-Me |
| 62 | 5-Me, 7-F | 4-Me |
| 63 | 5-Cl, 7-Me | 4-Me |
| 64 | 5,7-diCl | 3,4-diMe |
| 65 | 5-Me, 7-F | 3,4-diMe |
| 66 | 5-Cl, 7-Me | 3,4-diMe |
| 67 | 5-Cl, 7-F | 4-Cl |
| 68 | 5-CF₃O | 4-MeO, 3-Cl |

TABLE 2

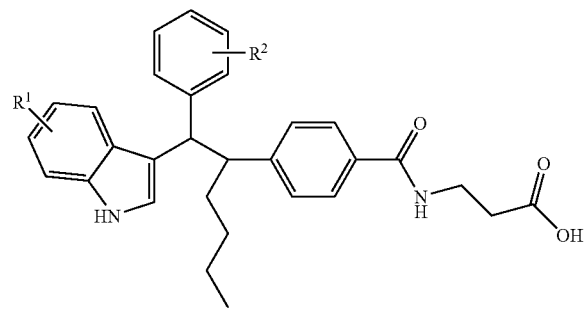

| EXAMPLE | R¹ | R² |
|---|---|---|
| 69 | 5-CF₃O | 4-MeO |
| 70 | 5,7-diCl | 4-MeO |
| 71 | 7-CF₃ | 4-MeO |
| 72 | 4,7-diCl | 4-MeO |
| 73 | 5,7-diF | 4-MeO |
| 74 | 7-Et | 4-MeO |
| 75 | 5-Cl, 7-Me | 4-MeO |
| 76 | 5-Bu, 7-Me | 4-MeO |
| 77 | 5-Me, 7-F | 4-MeO |
| 78 | 6,7-diCl | 4-MeO |
| 79 | 5,7-diCl | 4-Cl |
| 80 | 5-Me, 7-F | 4-Cl |
| 81 | 5-Me, 7-F | H |
| 82 | 5,7-diCl | 3,4-diF |

TABLE 3

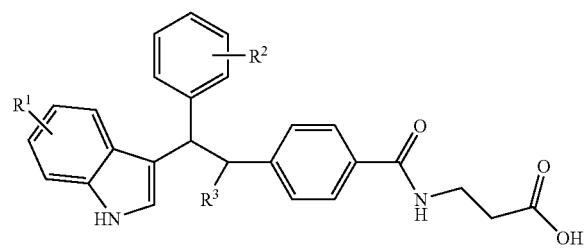

| EXAMPLE | R¹ | R² | R³ |
|---|---|---|---|
| 83 | 5-CF₃O | 4-Cl | Me |
| 84 | 5-CF₃O | 4-MeO | Me |
| 85 | 7-CF₃O | 4-Cl | Me |
| 86 | 6-CF₃O | 4-Cl | Me |
| 87 | 5-CF₃O | 4-MeO | Et |
| 88 | 5,7-diCl | 4-MeO | CF₃(CH₂)₃— (racemic) |
| 89 | 5,7-diCl | 4-Cl | Et |
| 90 | 5-Me, 7-F | 4-Cl | Et |

TABLE 4

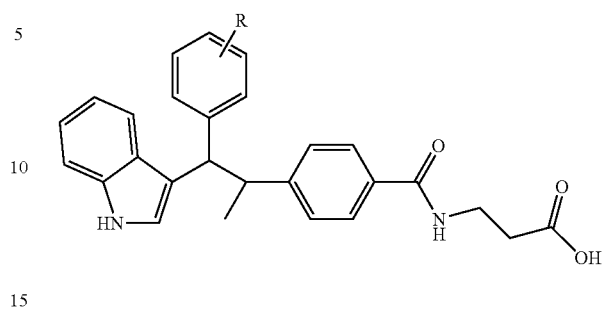

| EXAMPLE | R |
|---|---|
| 95 | 3-cyclohex-1-enyl |
| 96 | 3-cyclohexyl |
| 97 | 4-(4'-ᵗBu-cyclohex-1'-enyl) |
| 98 | 4-(4'-ᵗBu-cyclohexyl) |
| 99 | 4-hex-1-enyl |
| 100 | 4-hexyl |

TABLE 5

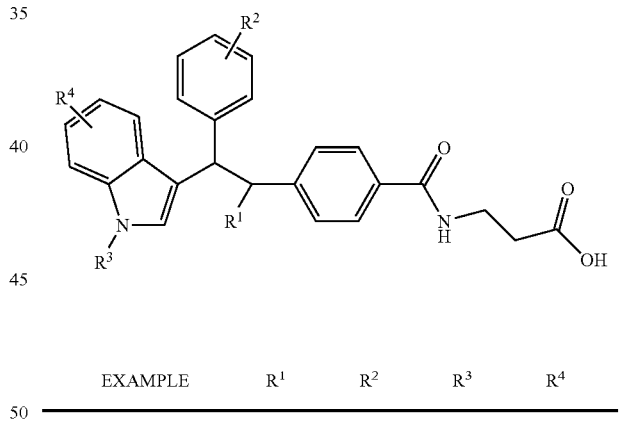

| EXAMPLE | R¹ | R² | R³ | R⁴ |
|---|---|---|---|---|
| 103 (racemic) | Me | 4-Cl | Bn | H |
| 104 (racemic) | n-Pr | 4-Cl | n-Pr | 5,7-diCl |
| 105 (enantiomer 1) | n-Pr | 4-CF₃O | Me | 5,7-diCl |
| 106 (enantiomer 2) | n-Pr | 4-CF₃O | Me | 5,7-diCl |
| 107 (enantiomer 1) | n-Bu | 4-MeO | Me | 5,7-diCl |
| 108 (enantiomer 2) | n-Bu | 4-MeO | Me | 5,7-diCl |

TABLE 6

[Structure with OMe-naphthyl, indole with R¹, phenyl-benzamide-NH-CH2CH2-COOH, and propyl group]

| EXAMPLE | R¹ |
|---------|-----|
| 109 | 7-Cl |
| 110 | 5-Cl |
| 111 | 5-CF$_3$O |
| 112 | 5,7-diCl |
| 113 | 6,7-diCl |
| 114 | 5-Me, 7-F |
| 115 | 7-CF$_3$ | or a pharmaceutically acceptable salt thereof.

13. A pharmaceutical composition comprising a compound in accordance with claim 1, or a pharmaceutically acceptable salt thereof, in combination with a pharmaceutically acceptable carrier.

14. A method of treating type 2 diabetes mellitus in a mammalian patient in need of such treatment comprising administering to said patient a compound in accordance with claim 1, or a pharmaceutically acceptable salt thereof in an amount that is therapeutically effective to treat said type 2 diabetes mellitus.

15. A method of treating hyperglycemia, diabetes or insulin resistance in a mammalian patient in need of such treatment which comprises administering to said patient a therapeutically effective amount of a compound in accordance with claim 1, or a pharmaceutically acceptable salt thereof.

16. A method of treating non-insulin dependent diabetes mellitus in a mammalian patient in need of such treatment comprising administering to the patient an anti-diabetic effective amount of a compound in accordance with claim 1, or a pharmaceutically acceptable salt thereof.

17. A compound of the structural formula:

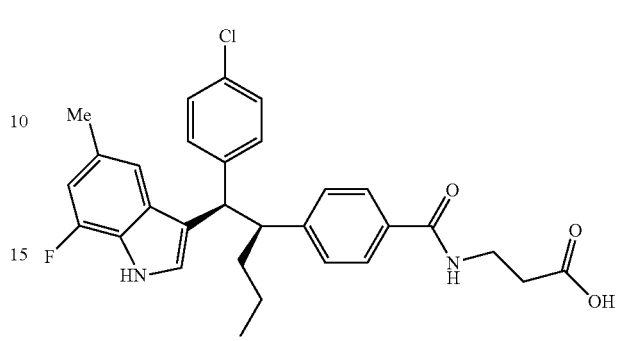

or a pharmaceutically acceptable salt thereof.

18. A compound of the structural formula:

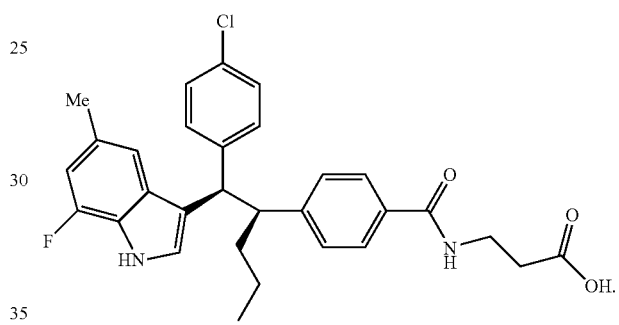

19. A pharmaceutical composition comprised of a compound in accordance with claim 17, or a pharmaceutically acceptable salt thereof, in combination with a pharmaceutically acceptable carrier.

20. A pharmaceutical composition comprised of a compound in accordance with claim 18 in combination with a pharmaceutically acceptable carrier.

* * * * *